United States Patent [19]

Natwick et al.

[11] Patent Number: 5,180,287
[45] Date of Patent: Jan. 19, 1993

[54] METHOD FOR MONITORING FLUID FLOW FROM A VOLUMETRIC PUMP

[75] Inventors: Vernon R. Natwick, Los Altos; Michael W. Lawless, Poway; Joseph E. Doll, Saratoga; Chung-You C. Wu, San Francisco, all of Calif.

[73] Assignee: Abbott Laboratories, Abbott Park, Ill.

[21] Appl. No.: 743,604

[22] Filed: Aug. 12, 1991

Related U.S. Application Data

[63] Continuation-in-part of Ser. No. 494,201, Mar. 15, 1990, Pat. No. 5,039,279.

[51] Int. Cl.⁵ ............................................. F04B 49/06
[52] U.S. Cl. ......................................... 417/43; 417/53; 417/63; 340/606
[58] Field of Search ............................ 417/43, 53, 63; 137/486; 340/606

[56] References Cited

U.S. PATENT DOCUMENTS

| | | | |
|---|---|---|---|
| 2,412,397 | 12/1946 | Harper | 103/148 |
| 3,609,069 | 9/1971 | Martinelli | 417/474 |
| 4,277,226 | 7/1981 | Archibald | 417/38 |
| 4,302,164 | 11/1981 | Manella | 417/474 |
| 4,391,600 | 7/1983 | Archibald | 604/153 |
| 4,443,671 | 4/1984 | Hinds | 340/606 |
| 4,479,797 | 10/1984 | Kobayashi et al. | 604/153 |
| 4,507,053 | 3/1985 | Frizzell | 417/43 |
| 4,559,038 | 12/1985 | Berg et al. | 604/153 |
| 4,650,469 | 3/1987 | Berg et al. | 604/131 |
| 4,653,987 | 3/1987 | Tsuji et al. | 417/360 |
| 4,690,673 | 9/1987 | Bloomquist | 604/67 |
| 4,728,265 | 3/1988 | Cannon | 417/363 |
| 4,915,591 | 4/1990 | Funke | 417/63 |
| 4,926,903 | 5/1990 | Kawai | 251/129.04 |

Primary Examiner—Michael Koczo
Assistant Examiner—David W. Scheuermann
Attorney, Agent, or Firm—Christensen, O'Connor, Johnson & Kindness

[57] ABSTRACT

A method for determining if fluid is being displaced by a volumetric pump. The volumetric pump (30) includes an inlet cracking valve (46) and an outlet cracking valve (52) disposed on opposite sides of a plunger (48) used to displace fluid by compressing flexible tubing (34). During a pumping segment of a pumping cycle for the volumetric pump, the outlet cracking valve is closed with a cracking force that compresses the flexible tubing until the pressure of the fluid displaced by the plunger exceeds a cracking pressure, at which time the outlet cracking valve opens to enable fluid flow from the volumetric pump. A cracking flexure (182) provides the cracking force. As the outlet cracking valve opens in response to the fluid pressure exceeding the cracking pressure, a flow detector (54) mounted to the cracking flexure responds to the stress generated in the cracking flexure thereby, producing a signal indicative of fluid flow from the volumetric pump. Since a compressible gaseous fluid in the pumping portion of the flexible tubing does not develop the cracking pressure, the flow detector also provides an indication when a source of liquid (31) for the volumetric pump has run dry. The method comprises the steps of processing the signal to determine if it exceeds a predefined threshold that varies as a function of the rate at which the pump is set to deliver fluid.

20 Claims, 15 Drawing Sheets

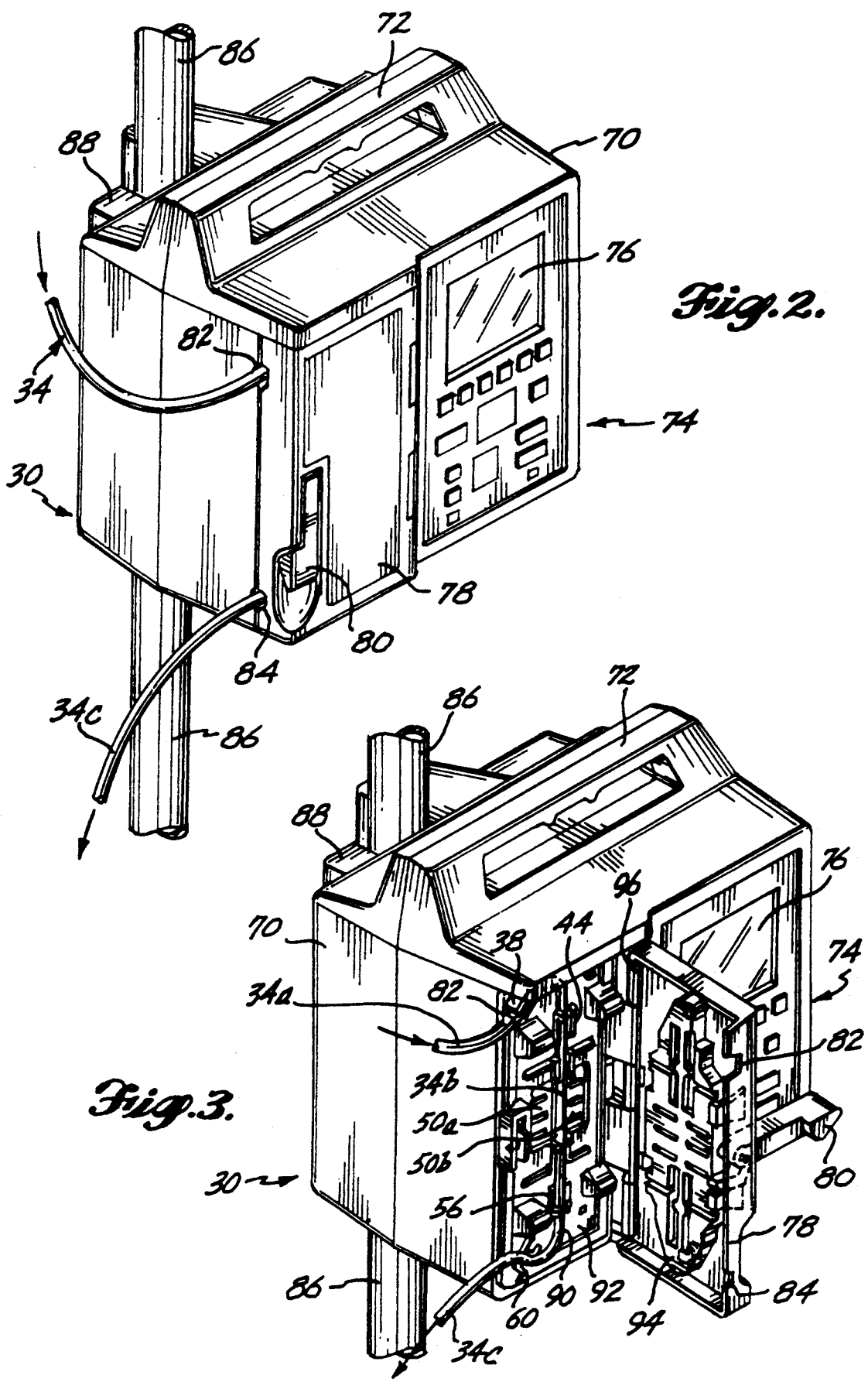

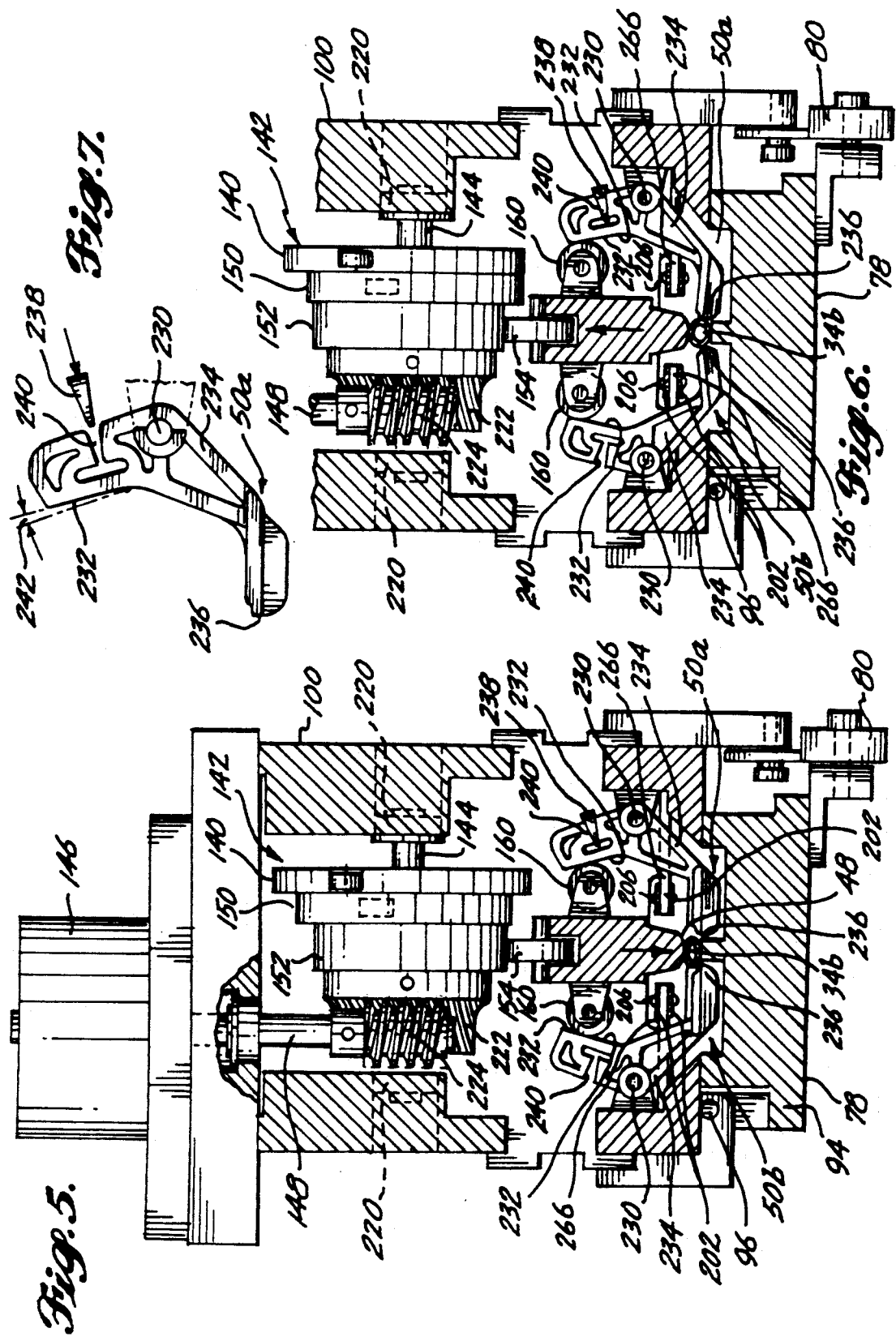

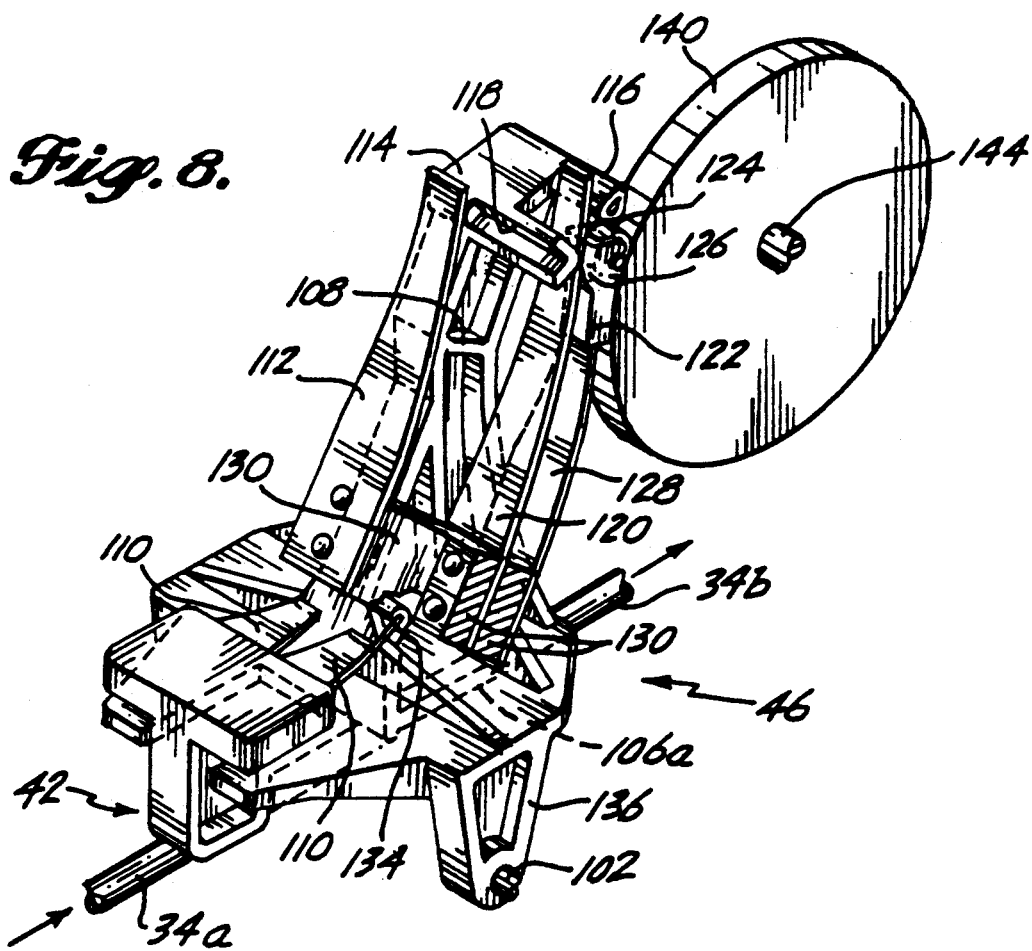
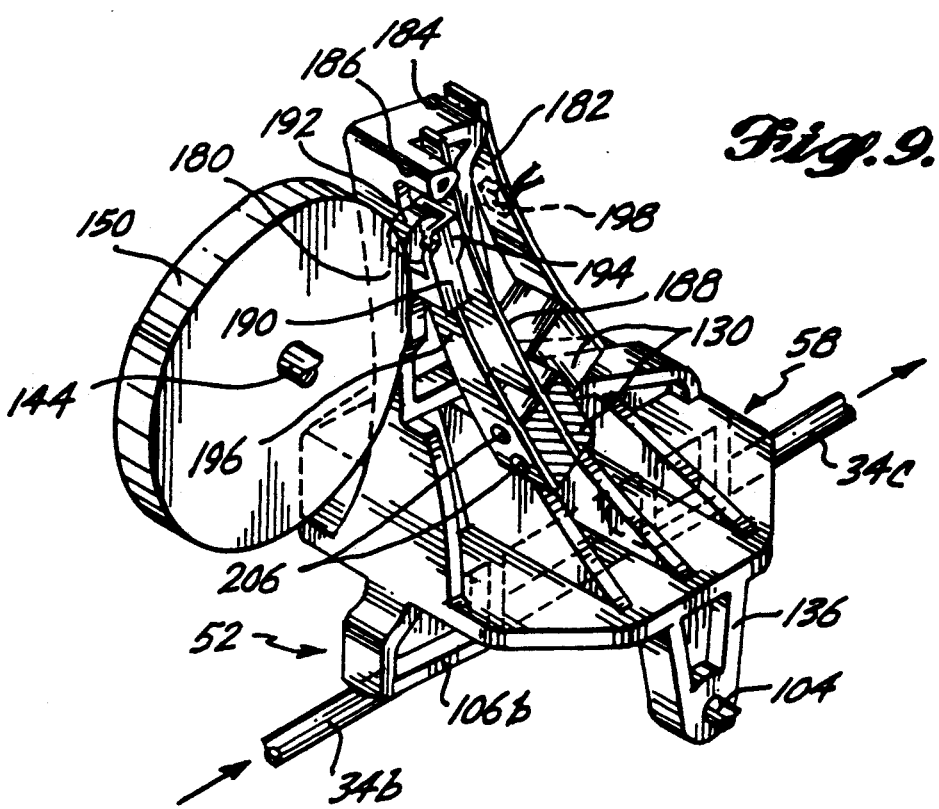

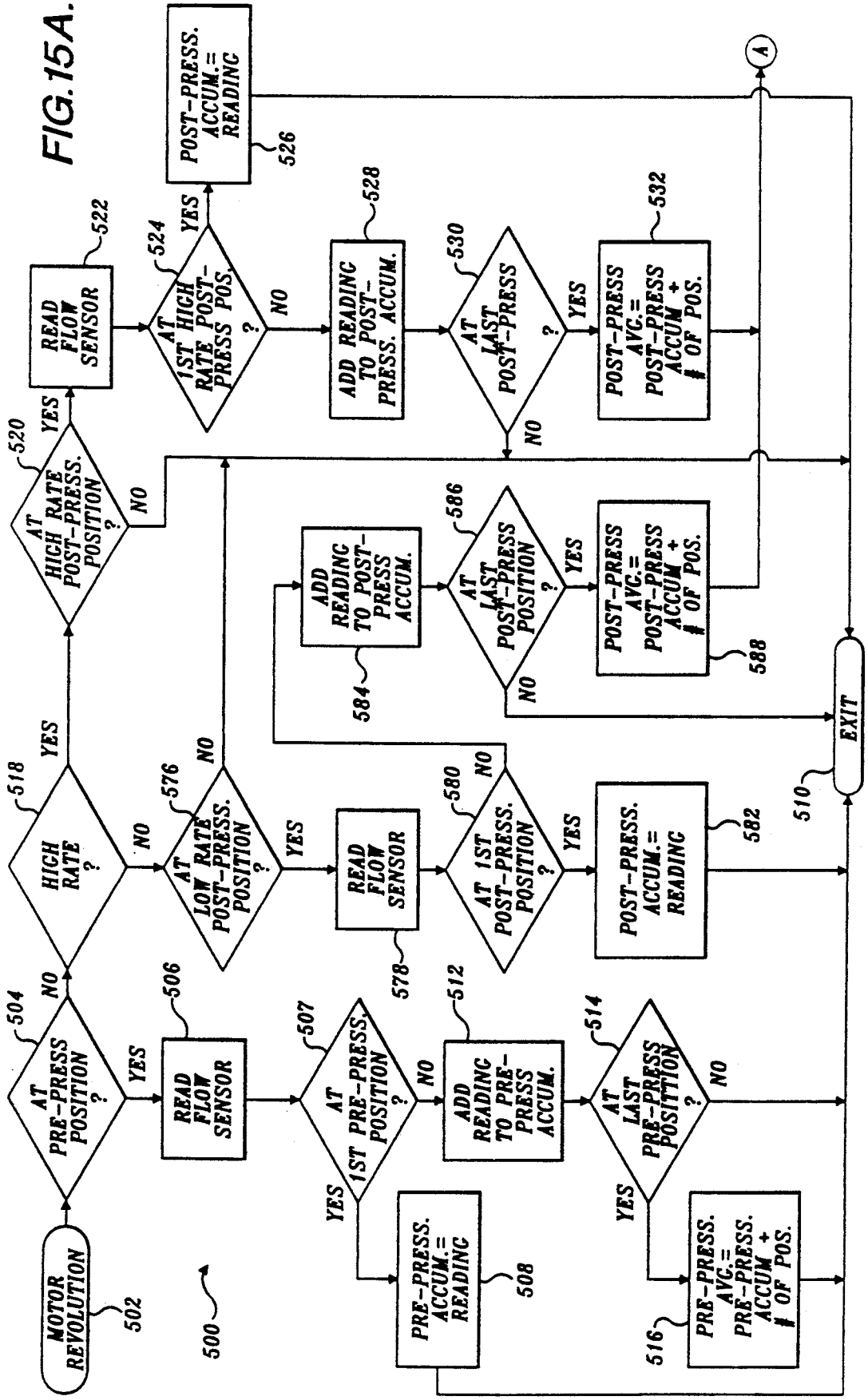

5,180,287

METHOD FOR MONITORING FLUID FLOW FROM A VOLUMETRIC PUMP

RELATED APPLICATIONS

This application is a continuation-in-part of pending commonly assigned prior U.S. patent application, Ser. No. 494,201, filed Mar. 15, 1990 U.S. Pat. No. 5,039,279. The benefit of the filing date of this prior application is hereby claimed under 35 U.S.C. section § 120.

FIELD OF THE INVENTION

This invention generally pertains to a method for monitoring the operation of a pump, and more specifically, to a method for monitoring a fluid flow condition related to the operation of a positive displacement pump.

BACKGROUND OF THE INVENTION

One of the important safety concerns that arises in the use of a pump to intravenously administer drugs to a patient is the need to insure that the medication is reaching the patient at the desired rate. Although medical personnel properly set the controls of an infusion pump to supply medication to the patient at the prescribed rate, the lines to and from the pump may become kinked or otherwise obstructed, for example, due to the patient rolling over onto a line. Many drug infusion pumps have fail-safe mechanisms to prevent drugs from being delivered to a patient at an excessive (e.g., free flow) rate, but only a few are provided with means for detecting a blockage in the delivery or supply lines. For detecting an obstruction of the supply line that leads from the drug container to the pump or for detecting that the drug container is empty, some pumps use drip detectors installed in the supply line immediately upstream of the pump inlet. However, connection of the drip detector adds to the time required to set up a drug infusion system, requires additional hardware, and makes the system more complex to use.

Another potential problem with this type of system concerns the infusion of excessive amounts of air into the patient's circulatory system. To prevent this condition, some infusion pumps include an air-in-line sensor that detects air bubbles larger than a specified size, e.g. larger than 100 microliters, since such bubbles can produce an air embolism in the patient's circulatory system that may be harmful. Air-in-line detectors typically monitor the fluid output of the pump using a matched resonant frequency ultrasonic piezoelectric transmitter and receiver that are disposed on opposite sides of a fluid passage in the pump. The ultrasonic piezoelectric transmitter applies an ultrasonic signal to one side of the fluid passage and the receiver monitors the level of that signal on the other side of the passage. Air bubbles in the fluid passage larger than the prescribed maximum size attenuate the ultrasonic signal that reaches the receiver, causing its output signal to fall below a predefined minimum level. A pump control circuit responds to the reduced output signal level caused by a large air bubble and shuts the pump off to prevent the air bubble from being infused into the patient. Additionally, an alarm is sounded to alert medical personnel that the pump has ceased operation, so that the problem causing the air bubbles can be corrected and operation of the pump restored to normal.

In addition to detecting air bubbles larger than a predefined size in the fluid administered using an infusion pump, an air-in-line sensor should ideally monitor the percentage of air being infused in the fluid, since many smaller air bubbles can coalesce to form a dangerous air embolism in the patient's circulatory system. For example, if the air-in-line sensor detects that more than ten (10) percent of the infused fluid comprises air, the pump should be stopped and an alarm sounded so that the condition causing the small air bubbles can be corrected. However, air-in-line sensors that must be calibrated to respond to a wide range of air bubble sizes are more likely to produce false alarms and to be less accurate in determining the percentage of air infused in the form of small bubbles. It would be preferable to use a different mechanism to prevent relatively larger volumes of air from being infused into a patient.

In consideration of each of the above-described problems, it is an object of this invention to provide a method for detecting whether fluid is flowing through a positive displacement pump. It is a further object to use a signal produced by a sensor integral to the pump in this method, to detect that a supply container for the fluid is empty, or to detect that a supply line from the container is blocked, preventing the fluid reaching the inlet of the pump. Yet a further object is to provide a method for detecting the presence of a substantial volume of air or other gaseous fluid in a pumping chamber of the pump in order to prevent the volume of gaseous fluid being forced from the pump. A still further object of the method is to provide an alarm if the pump is operating, but is not pumping fluid from the pumping chamber.

The foregoing aspects and advantages of this invention will become apparent by reference to the accompanying drawings and the Detailed Description of the Preferred Embodiment that follows.

SUMMARY OF THE INVENTION

In accordance with the present invention, a method is provided for determining whether a fluid is flowing from a positive displacement pump. The pump includes an outlet valve that opens to allow fluid to flow past it during a pumping cycle when a fluid pressure within the pump reaches a predefined cracking pressure. Steps carried out in the method include producing a signal indicative of a movement of the outlet valve from a closed position to at least a partially open position that allows fluid to flow from the pump, in response to the fluid pressure within the pump exceeding the predefined cracking pressure. A threshold for the signal is established, and the signal is compared to the threshold. Based upon the relative magnitudes of the signal and the threshold, a determination of whether fluid is flow from the pump is made.

To establish the threshold, a pre-pressurization level of the signal is determined during the pumping cycle, at a first time interval that is substantially prior to pressurizing the fluid to the cracking pressure. Likewise, a post-pressurization level of the signal is determined during the pumping cycle, at a second time interval that is substantially after pressurizing the fluid to the cracking pressure. The threshold is a function of a difference between the post-pressurization level and the pre-pressurization level.

Preferably, the pre-pressurization level is an average of a plurality of pre-pressurization readings taken at a plurality of times during the first time interval, and the post-pressurization level is an average of a plurality of post-pressurization readings taken at a plurality of times during the second time interval. The method can further comprise the step of compensating the threshold for variations in the signal as a function of a rate at which the pump delivers fluid.

As a further step, the method provides for producing an alarm signal if the relative magnitude of the signal and the threshold indicates that fluid is not flowing from the pump. The step of producing the alarm signal can be arranged to occur only if the relative magnitude of the signal and the threshold indicates that fluid is not flowing from the pump for a plurality of pumping cycles. In addition, the method can provide for determining whether fluid is not flowing from the pump due to an occlusion or due to the presence of a substantial volume of a gaseous fluid in the pump. In this instance, pressurization of a substantially gaseous fluid with the pump can not develop a fluid pressure in excess of the cracking pressure so that when the substantially gaseous fluid enters the pump, fluid flow from the pump is interrupted.

To produce the signal, stress in a flexure that biases the outlet valve closed can be monitored to detect when the fluid pressure in the pump has exceeded the cracking pressure, causing fluid to flow from the pump by elastically deforming the flexure. However, other flow sensing devices are contemplated for use in practicing the method.

BRIEF DESCRIPTION OF THE DRAWINGS

FIG. 2 is an isometric view of the volumetric pump, showing an access door that is closed and latched in place;

FIG. 3 is an isometric view, similar to that shown in FIG. 2, but with the access door shown in an open position, disclosing the path followed by flexible tubing through the volumetric pump;

FIG. 5 is a schematic transverse cross section of the volumetric pump, illustrating compression of the flexible tubing to pump fluid;

FIG. 6 is a schematic cross section of the volumetric pump, illustrating reshaping of the flexible tubing to facilitate its filling with fluid;

FIG. 7 is a plan view illustrating the calibration of one of the tube reshaping arms to achieve a desired angular deflection;

FIG. 8 is an isometric view of an inlet cracking valve used in the volumetric pump and a transverse section of a cam assembly that is used to actuate the cracking valve;

FIG. 9 is an analogous view to that of FIG. 8, isometrically showing an outlet cracking valve used in the volumetric pump and a transverse section of the cam assembly that is used to actuate the outlet cracking valve, and also showing how a sensor used in connection with the present invention is disposed to produce a signal indicative of fluid flow past the outlet cracking valve;

FIGS. 15A and 15B comprise a flow chart illustrating the steps implemented by the volumetric pump controller in determining whether fluid is flowing from the volumetric pump;

DETAILED DESCRIPTION OF THE PREFERRED EMBODIMENT

Volumetric Pump

The term "volumetric pump" is applied to a positive displacement pump with which the present invention is used because it appropriately emphasizes one of the more important advantages of this pump. Specifically, during each pumping stroke, the volumetric pump consistently and repeatedly displaces a defined volume of fluid at a defined pressure, thereby ensuring that a desired rate of fluid flow is accurately provided by the pump. The present invention is used with the volumetric pump to monitor its operation and to provide an alarm in the event that fluid flow from the volumetric pump is interrupted, either due to an interruption of the fluid flow path proximal or distal of the volumetric pump or because relatively large air bubbles have entered the volumetric pump.

Figure 1:
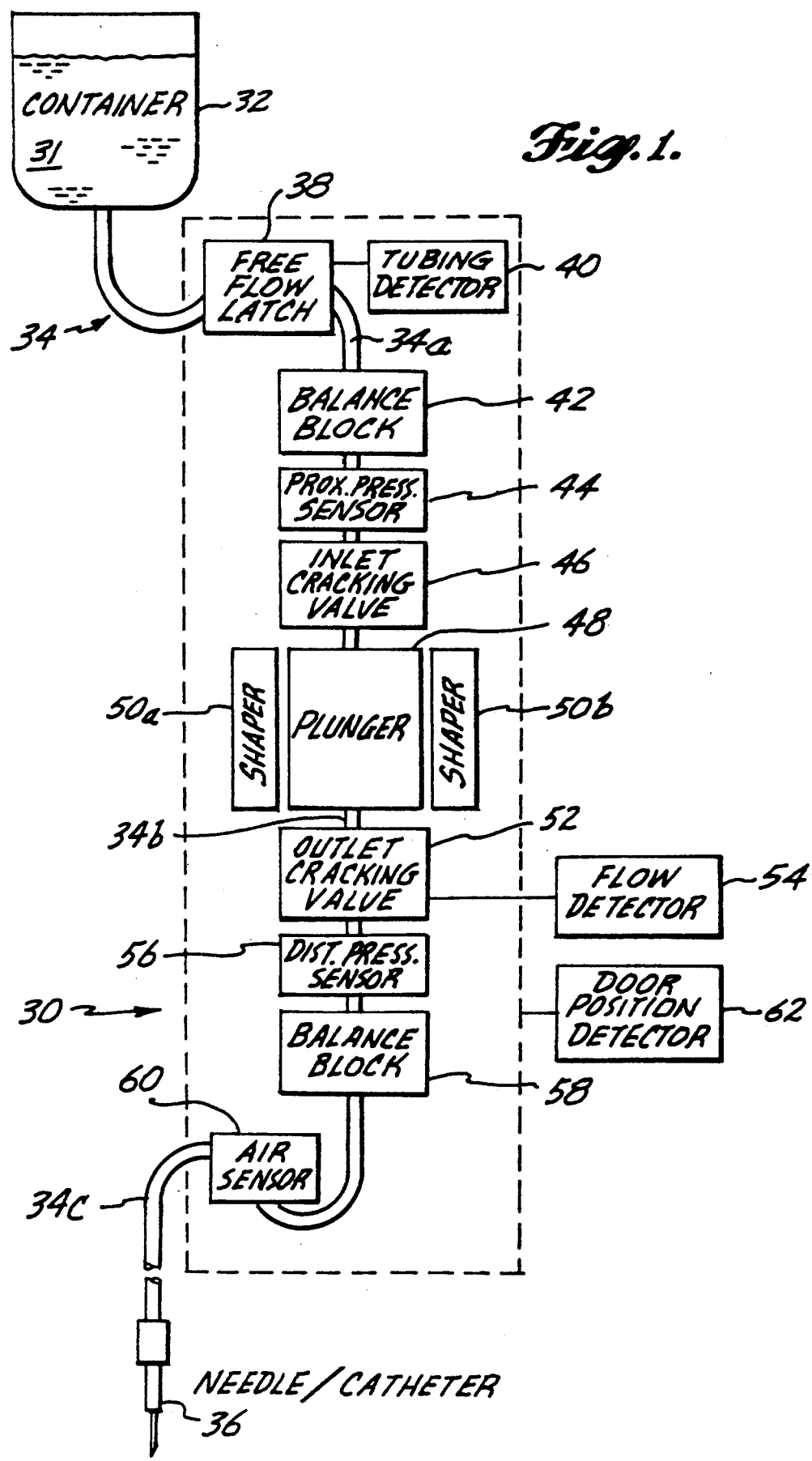
FIG. 1 is a schematic block diagram of a volumetric pump in which the present invention is used.

In FIG. 1, a volumetric pump is generally illustrated in a block diagram at reference numeral 30. Volumetric pump 30 comprises a number of components that are serially arranged along a fluid path through the pump. A liquid 31 that is administered by volumetric pump 30 is supplied from a container 32 through flexible tubing 34. Liquid 31 enters volumetric pump 30 through a proximal portion 34a of the flexible tubing. The fluid path continues through a pumping portion 34b and exits the pump through a distal portion 34c of the flexible tubing. Distal portion 34c of the flexible tubing is connected to a needle/catheter 36 that is used to introduce liquid 31 output from the pump intravenously into a patient. Of course, volumetric pump 30 may also be used in other applications wherein distal portion 34c of the flexible tubing is connected to some other apparatus disposed downstream of volumetric pump 30.

Flexible tubing 34 is continuous, but for purposes of this disclosure, is referred to as divided into the proximal, pumping, and distal portions 34a, 34b, and 34c, respectively; preferably, the flexible tubing comprises a polyvinyl chloride (PVC) disposable tube set, such as is customarily used to administer fluids intravenously to a patient. The tubing may have a 0.137" O.D. and 0.100" I.D.

In this application of the volumetric pump, it is desirable to prevent free flow of liquid 31 from container 32 into the patient. For this reason, volumetric pump 30 includes a free flow latch 38, which clamps proximal portion 34a of the flexible tubing to prevent liquid 31 from container 32 flowing freely into a patient, due to head pressure. Free flow latch 38 does not restrict fluid flow during the normal pumping operation of volumetric pump 30, but is configured to automatically clamp proximal portion 34a of the flexible tubing when a door 78 (shown in FIGS. 2 and 3) on volumetric pump 30 is opened. While door 78 is closed, free fluid flow through volumetric pump 30 is otherwise precluded by volumetric pump 30, as explained below. The position of door 78 is sensed by a door position detector 62, producing a signal that prevents operation of volumetric pump 30 when door 78 is open. Similarly, a tubing detector 40 is interconnected to free flow latch 38, and produces a signal indicative of the presence of flexible tubing 34 within free flow latch 38; operation of volumetric pump 30 is inhibited if the signal indicates that the flexible tubing is not in place.

A balance block 42 rests against proximal portion 34a of flexible tubing 34 and serves to compensate for variations or changes in the elasticity of flexible tubing 34. The function and operation of balance block 42 are more fully explained below.

Next in the serial arrangement of components along the fluid path within volumetric pump 30 is a proximal pressure sensor 44, which operates to sense the pressure of fluid within proximal portion 34a of the flexible tubing. Proximal pressure sensor 44 produces a signal indicative of fluid pressure in this portion of flexible tubing 34 for use in monitoring the operation of the pump and serves as a further means to determine if proximal portion 34a has become occluded.

An inlet cracking valve 46 is disposed immediately downstream of proximal pressure sensor 44. Inlet cracking valve 46 functions in cooperation with a plunger 48 and an outlet cracking valve 52, which are disposed sequentially downstream of the inlet cracking valve, to displace a volumetric quantity of fluid from pumping portion 34b of the flexible tubing and to generally isolate the volumetric pump from variations in proximal and distal fluid pressure, due, for example, to variations in the elevation of container 32, or variations in the back pressure of fluid in distal portion 34c of the flexible tubing. Tubing shapers 50a and 50b are disposed at each side of plunger 48 and act to rapidly reform pumping portion 34b of the flexible tubing as it refills with fluid during each pump cycle, insuring consistent volumetric refill with each pumping stroke.

A flow detector 54 that is used in connection with the present invention is functionally connected with outlet cracking valve 52. Flow detector 54 produces a signal indicating whether fluid is successfully being pumped by volumetric pump 30 into distal portion 34c of the flexible tubing. The present invention thus comprises a method of using this signal to detect fluid flow from the volumetric pump. As explained below, in response to an alarm that is sounded if the method detects insufficient fluid flow, medical personnel are alerted to correct the causal condition. For example, if container 31 has become empty of liquid 31 or if a kink in the flexible tubing has prevented fluid flow from volumetric pump 30, the medical personnel can supply a new container or straighten the kinked tubing, once alerted by the alarm.

A distal pressure sensor 56 produces a signal indicative of the fluid pressure within distal portion 34c of the flexible tubing, i.e., the output pressure of volumetric pump 30. The distal fluid pressure is used for monitoring the operation of volumetric pump 30 and for sensing an occlusion of flexible tubing 34.

Immediately adjacent distal pressure sensor 56 is a balance block 58. Cooperating with outlet cracking valve 52, balance block 58 compensates for changes or variations in the stiffness or elasticity of flexible tubing 34, in a manner similar to that in which balance block 42 cooperates with inlet cracking valve 46.

An air sensor 60 is the last component along the fluid path through volumetric pump 30. Air sensor 60 detects the presence of air bubbles larger than a predefined volume (or percent of the fluid volume being delivered) in the fluid discharged from the volumetric pump, and produces a signal indicative of such air bubbles. This signal stops volumetric pump 30 and initiates an alarm to prevent a potentially harmful air embolism forming in the fluid being introduced into a patient through needle/catheter 36. Air sensor 60 comprises a generally conventional piezoelectric ultrasonic transmitter and receiver (not separately shown), spaced apart on opposite sides of distal portion 34c of the flexible tubing. The transmitter produces an ultrasonic signal that is transmitted through flexible tubing 34 to the receiver. Liquid present in flexible tubing 34 between the transmitter and receiver conveys the ultrasonic signal much more efficiently than does an air bubble. The receiver produces an electronic signal in response to the level of the ultrasonic signal reaching it, the amplitude of the electronic signal indicating whether an air bubble or liquid is present in flexible tubing 34 between the transmitter and receiver. Details of air sensor 60 are not illustrated because such devices are generally well known to those of ordinary skill in this art.

Proximal pressure sensor 44, distal pressure sensor 56, air sensor 60, and flow detector 54 form a complete monitoring system to ensure that volumetric pump 30 is operating properly. To some extent, these components have redundant functions, but flow detector 54 serves as a final back-up for the monitoring system, since it provides a signal used by the present invention to detect whether the volumetric pump is performing its primary function, i.e., pumping liquid 31.

In FIGS. 2 and 3, volumetric pump 30 is illustrated in isometric view. As shown therein, volumetric pump 30 includes a molded plastic housing 70, having a handle 72 on its upper surface to facilitate carrying the volumetric pump to a point of use. A control panel 74 and a display 76 are disposed on the right side of the front surface of volumetric pump 30, and are respectively used by an operator for entry and display of data that controls the volumetric pump and for displaying the cause of an alarm condition.

On the back of housing 70 is formed a clamp 88, by which volumetric pump 30 is removably attached to a post 86, for example, at the bedside of a patient. Details of clamp 88 are not shown, since it is generally typical of those used with other types of medical apparatus intended for connection to vertical posts.

In FIG. 2, door 78 is shown latched closed, the appropriate disposition for use of the volumetric pump, while in FIG. 3, door 78 is shown in an open position. A latch handle 80 is pivoted upwardly so that door 78 can be swung open on a hinge 96, giving access to an inner cover 92 that defines the path followed by flexible tubing 34 through volumetric pump 30. As noted above, when door 78 is opened while flexible tubing 34 is threaded through the volumetric pump and connected to container 32, free flow latch 38 clamps the flexible tubing closed to prevent liquid 31 in container 32 from free flowing through flexible tubing 34. The mechanism that actuates free flow latch 38 when door 78 is opened is not shown since it is not particularly relevant to the present invention.

Flexible tubing 34 is angled upwardly where it passes through an entry slot 82 formed on the side of door 78, insuring that any of liquid 31 leaking from container 32 drips from a loop formed in flexible tubing 34 and does not run into volumetric pump 30. After door 78 is swung open, flexible tubing 34 is readily threaded into a channel 90 defined along the longitudinal center of inner cover 92. An exit slot 84, formed in the lower side portion of door 78, overlies distal portion 34c of the flexible tubing. A pressure plate 94 disposed on the inner surface of door 78 comes into contact with flexible tubing 34 along the length of channel 90 as door 78 is closed and latched with handle 80.

Figure 4:
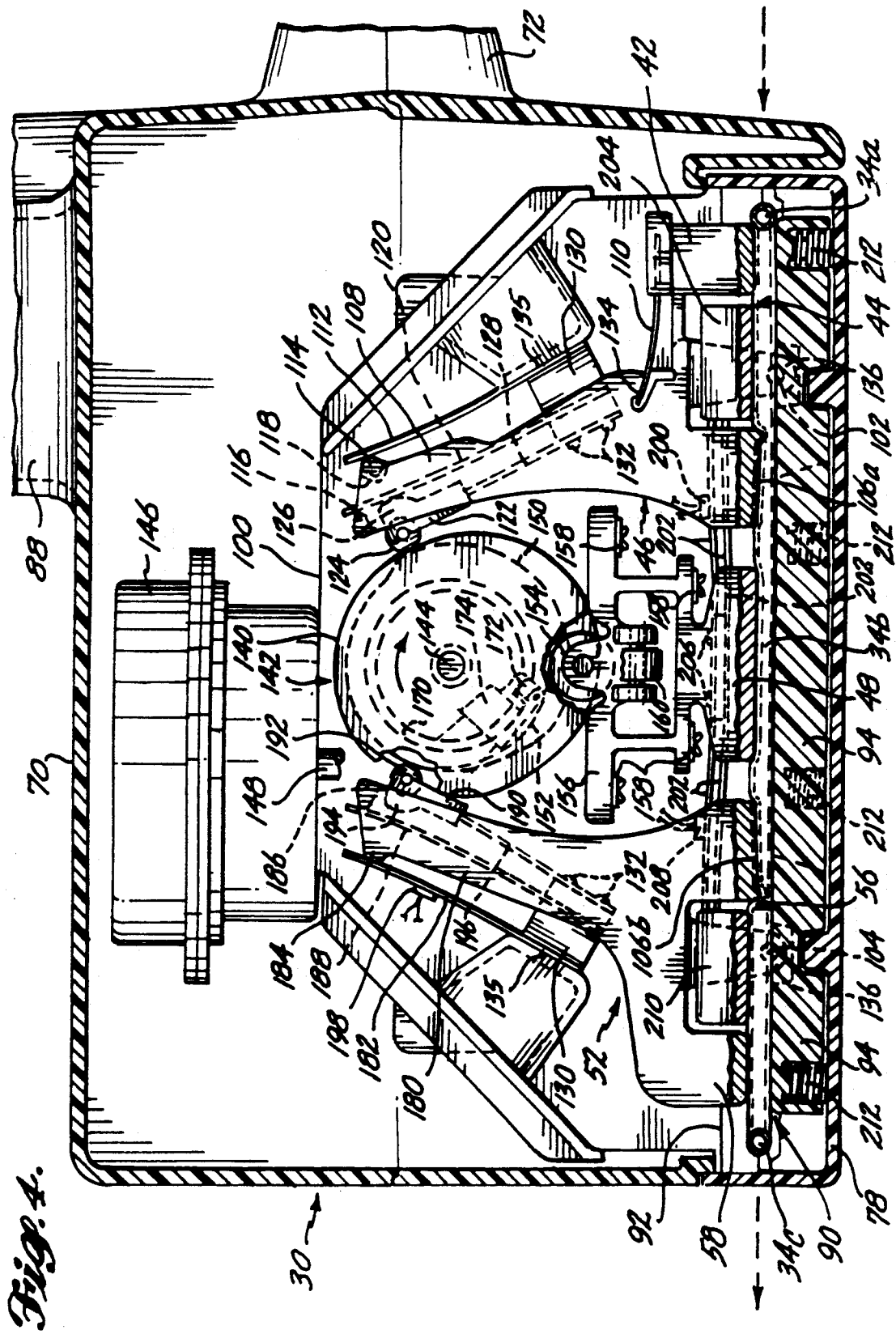
FIG. 4 is a longitudinal cross section of the pump assembly shown in FIGS. 2 and 3.
Figure 10A:
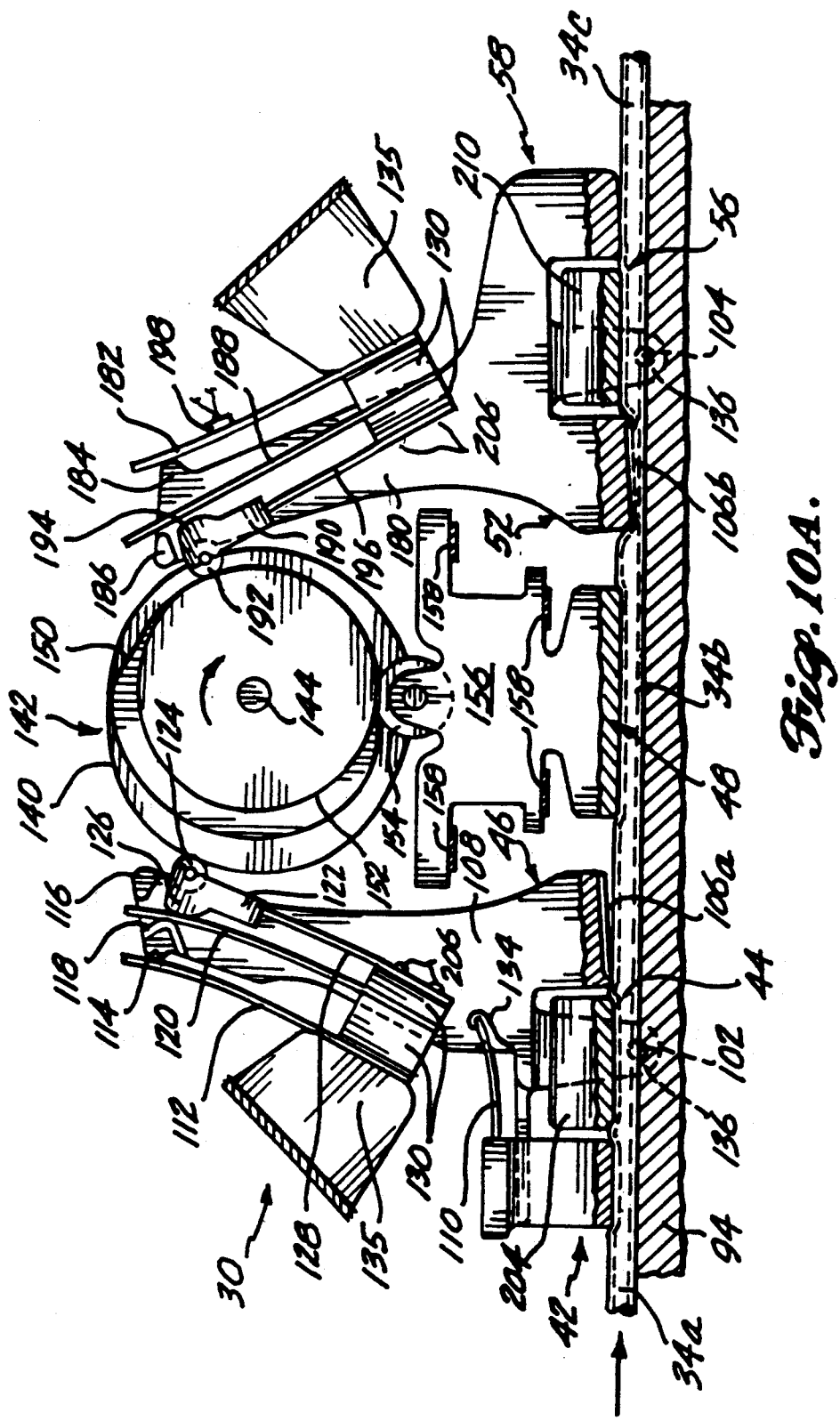
FIGS. 10A-10C are cutaway, longitudinal cross sections of the volumetric pump respectively illustrating a fill segment, a pumpback-pressurization segment, and a pumping segment of its pumping cycle.
Figure 10B:
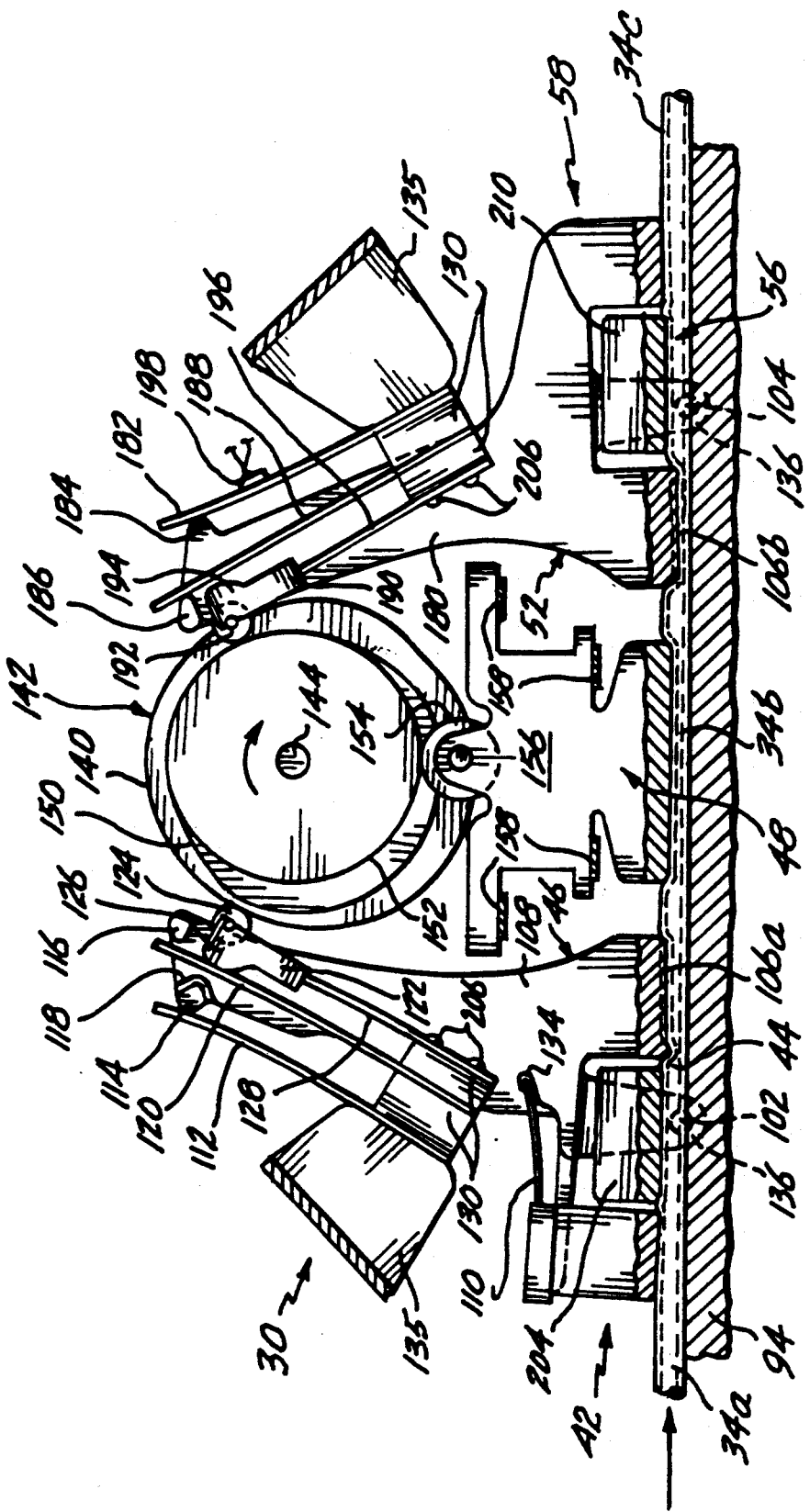
Figure 10C:
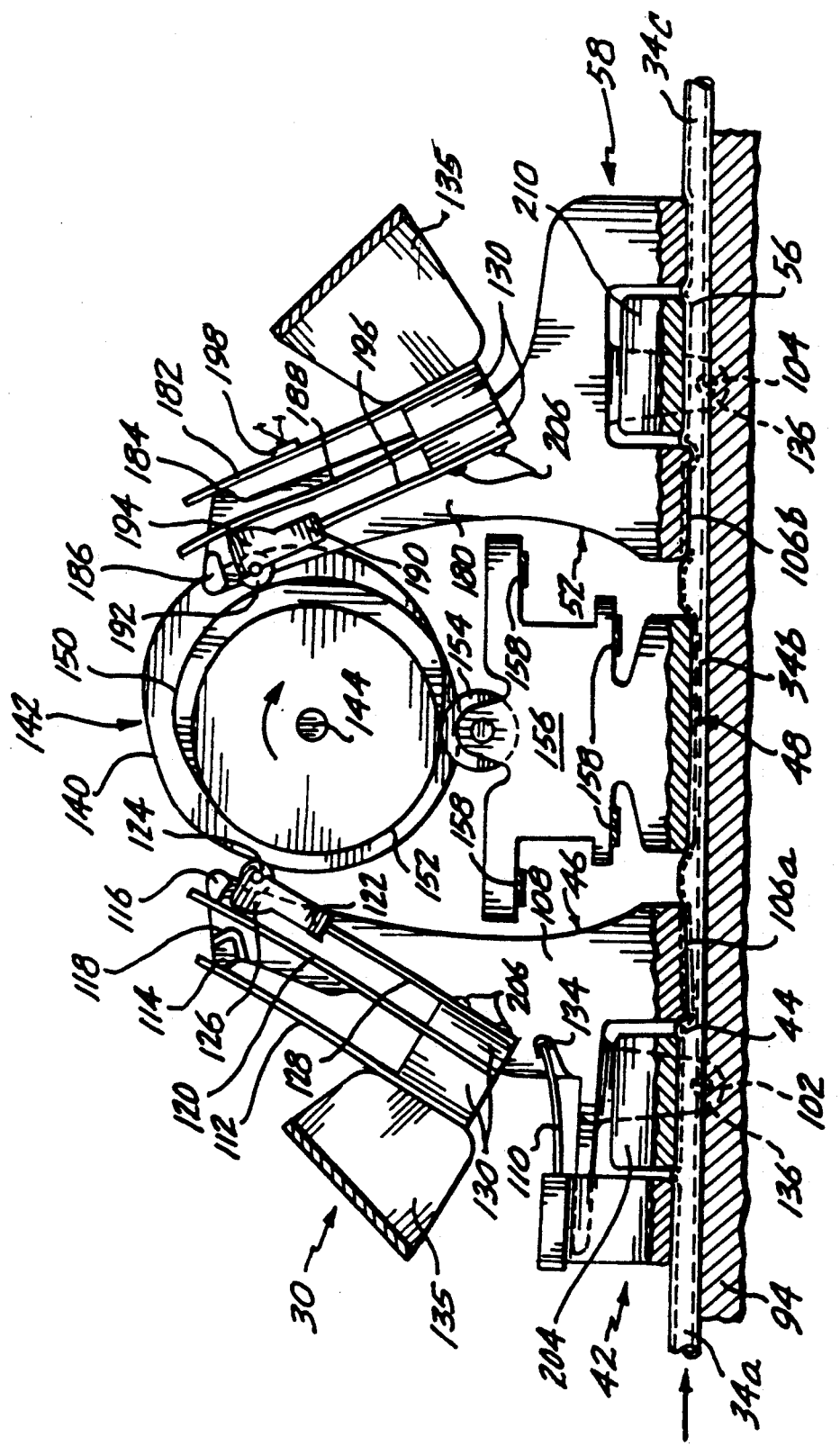

FIGS. 4, 5, and 6 show details of the interior of volumetric pump 30. Pressure plate 94 defines a reference plane or surface in respect to each of the components of volumetric pump 30 that act to compress flexible tubing 34 and is mounted so that it floats on a plurality of helical coiled springs 212. Springs 212 bias pressure plate 94 away from the inner surface of door 78. When door 78 is closed, pressure plate 94 contacts inner cover 92 at several points. Helical springs 212, which are relatively stiff, are thus slightly compressed, and therefore accommodate variations in the tolerances of door 78 and other related parts that arise during construction of volumetric pump 30. Such tolerances might otherwise affect the position of the reference plane defined by pressure plate 94.

Most of the components comprising volumetric pump 30 are mounted on a frame 100 within housing 70. For example, frame 100 includes inlet cracking valve pivot mounts 102 and outlet cracking valve pivot mounts 104, about which inlet cracking valve 46 and outlet cracking valve 52 respectively pivot.

Inlet cracking valve 46 contacts proximal portion 34a of the flexible tubing along a valve face 106a. Similarly, outlet cracking valve 52 contacts distal portion 34c of the flexible tubing along a valve face 106b. The pivotal motion of inlet cracking valve 46 and outlet cracking valve 52 respectively varies the force with which valve faces 106a and 106b contact flexible tubing 34 to control fluid flow therethrough by compressing the flexible tubing against pressure plate 94. Plunger 48 compresses pumping portion 34b of the flexible tubing against pressure plate 94 to displace fluid from within a pumping chamber defined between the inlet and outlet cracking valves 46 and 52. In part because volumetric pump 30 includes inlet and outlet cracking valves 46 and 52, it operates differently than the prior art plunger type peristaltic pumps, as will be apparent from the following disclosure.

An inlet valve arm 108 extends upwardly from valve face 106a on inlet cracking valve 46. Disposed generally above inlet cracking valve pivot mounts 102 are flat metal spring flexures 110, which connect balance block 42 to a slot 134, formed on the back side of inlet valve arm 108. Flexures 110 are snapped within slot 134 and flex to enable inlet valve arm 108 to pivot valve face 106a away from pressure plate 94 through a greater angle than would otherwise be possible, without closing off fluid flow through flexible tubing 34 due to compression of the flexible tubing by balance block 42. Inlet cracking valve pivot mounts 102 are connected to downwardly depending pivot arms 136 on inlet cracking valve 46, at each side of flexible tubing 34, and are centered between balance block 42 and valve face 106a. The stiffness of flexible tubing 34 acts on balance block 42 and flexures 110, and the balance force developed as a function of this stiffness (or lack of elasticity) tends to pivot inlet valve face 106a against pressure plate 94, thereby increasing the force exerted by that part of inlet cracking valve 46 to compress the flexible tubing. The stiffness of flexible tubing 34 also resists compression by inlet valve face 106a to a similar extent. Accordingly, variations in the elasticity of flexible tubing 34 that affect the force required for inlet valve face 106a to compress the tubing are automatically compensated for by balance block 42.

Inlet cracking valve 46 operates in three distinct modes, the force applied by valve face 106a to compress flexible tubing 34 being substantially different in each mode. Two different spring-bias forces act on inlet valve arm 108. A fluid flow control force is applied to inlet valve arm 108 by a flat metal spring cracking flexure 112, acting against a knob 114, which is disposed at one end of inlet valve arm 108. The additional force necessary to compress flexible tubing 34 sufficiently to completely close off fluid flow past inlet cracking valve 46 is supplied by a flat metal spring closure flexure 120. Closure flexure 120 acts upon a side arm 116, disposed on one side of inlet valve arm 108. The combined force provided by cracking flexure 112 and closure flexure 120 (in addition to the balance force provided by balance block 42) pivots inlet cracking valve 46 about a pivot axis extending through inlet cracking valve pivot mounts 102, to completely block fluid flow through flexible tubing 34.

An inlet valve cam follower 122 selectively determines whether cracking flexure 112 and closure flexure 120 apply force against inlet valve arm 108 and thus determines the three modes in which inlet cracking valve 42 operates. Inlet valve cam follower 122 includes a roller 124 rotatably mounted in a hood 126, which is attached via an inlet follower flexure 128 to a plurality of blocks 130. Blocks 130 are also used in mounting cracking flexure 112 and closure flexure 120 to a bracket 135 and to provide appropriate spacing between these flexures and bracket 135. Bolts 132 connect the ends of each of these flexures to bracket 135, which comprises a portion of frame 100.

Roller 124 rolls along an inlet valve cam track 140, disposed on a rotating cam assembly 142. Cam assembly 142 turns on a camshaft 144, which at each of its ends is mounted to frame 100 in bearings 200 (see FIGS. 5 and 6). A motor shaft 148 extends downwardly from a motor 146, and a helical gear 224 on motor shaft 148 drivingly engages gear teeth 222, which are formed on one end of cam assembly 142, causing the cam assembly to rotate in a clockwise direction, as viewed in FIG. 4. The radial distance between camshaft 144 and the point where roller 124 contacts the surface of inlet valve cam track 140 varies as cam assembly 142 rotates, moving inlet valve cam follower 122 radially back and forth so as to control the forces applied to inlet valve arm 108. Specifically, as hood 126 is forced radially back against closure flexure 120, it lifts the closure flexure away from side arm 116, eliminating the force normally exerted by the closure flexure against the side arm and thereby reducing the total force exerted by valve face 106a against flexible tubing 34. In this configuration, inlet cracking valve 46 is in a "cracking mode."

As hood 126 moves further radially outward, closure flexure 120 contacts a "V-shaped" side arm 118 that is formed on the side of inlet valve arm 108, causing inlet valve arm 108 to pivot valve face 106a away from pressure plate 94. In this configuration, inlet cracking valve 46 is in an open mode, wherein liquid 31 freely flows from container 32 through proximal portion 34a of the flexible tubing and into pumping portion 34b. Flexures 110 bend as valve face 106a pivots away from pressure plate 94, so that balance block 42 does not close off fluid flow through proximal portion 34a of the flexible tubing.

When both closure flexure 120 and cracking flexure 112 are allowed to act on inlet valve arm 108, valve face 106a compresses flexible tubing 34 against pressure plate 94 sufficiently to completely block fluid flow through the flexible tubing. In this configuration, inlet cracking valve 46 is in a "closed mode."

An outlet valve cam track 150 is disposed between inlet valve cam track 140 and a plunger cam track 152. Plunger cam track 152 provides a surface at varying radii about camshaft 144 for actuating plunger 48 to compress pumping portion 34b of the flexible tubing against pressure plate 94. A roller 154 is rotatably mounted on a base 156 of plunger 48, and is thus disposed to roll along plunger cam track 152. Also mounted on base 156, at opposite sides of roller 154, are tubing shaper rollers 160. The disposition of tubing shaper rollers 160 is more clearly shown in FIGS. 5 and 6, and their operation in respect to shaping flexible tubing 34 is disclosed in detail below.

As shown using hidden lines in FIG. 4, the back side of cam assembly 142 includes a torque compensation track 170. A conically-shaped torque compensation roller 172 rolls along torque compensation track 170, applying a rotational torque to cam assembly 142 that compensates for an opposite torque resulting from rapid changes in the shape of inlet valve cam track 140, outlet valve cam track 150, and plunger cam track 152. Torque compensation roller 172 is mounted on a flat metal spring torque compensation flexure 174 that applies a biasing force to cam assembly 142.

Like inlet cracking valve 46, outlet cracking valve 52 has a generally "Y-shaped" configuration and includes an outlet valve arm 180, which is connected to outlet valve face 106b and to balance block 58. On opposite sides of flexible tubing 34, pivot arms 136 extend downwardly, connecting to outlet cracking valve pivot mounts 104 on frame 100. Balance block 58 rests on distal portion 34c of the flexible tubing and develops a force proportional to the stiffness (or lack of elasticity) of flexible tubing 34, which tends to increase the compression force applied against flexible tubing 34 by outlet valve face 106b to compensate or balance the resistance to compression caused by the stiffness (or lack of elasticity) of the flexible tubing. Just as balance block 42 compensates for changes or variations in elasticity of the flexible tubing in respect to inlet cracking valve 46, balance block 58 compensates for such changes and variations in respect to outlet cracking valve 52. However, since outlet cracking valve 52 is never pivoted to an open mode like inlet cracking valve 46, balance block 58 is integrally attached to outlet valve arm 180. Flexures 110 are not required, since the extent of pivotal rotation of outlet cracking valve 52 is substantially more limited than for inlet cracking valve 46. At all times, even when volumetric pump 30 is not pumping fluid, either inlet cracking valve 46 or outlet cracking valve 52 is in its closed mode, preventing liquid 31 from free flowing through flexible tubing 34.

As shown in FIG. 4, outlet cracking valve 52 is in its closed mode, compressing flexible tubing 34 against pressure plate 94 sufficiently to block fluid flow therethrough. In this configuration, a flat metal spring cracking flexure 182 applies force against a knob 184 on the top of outlet valve arm 180. In addition, a flat metal spring closure flexure 188 applies a biasing force against a side arm 186 that extends outwardly from the side of outlet valve arm 180.

An outlet valve cam follower 190 includes a roller 192, which rolls along outlet valve cam track 150. Roller 192 is rotatably mounted within a hood 194, which is connected to a flat metal spring follower flexure 196. Follower flexure 196 spring biases roller 192 into contact with outlet valve cam track 150. The lower ends of follower flexure 196, cracking flexure 182, and closure flexure 188 are all secured at blocks 130 to bracket 135 by bolts 132, just as the corresponding elements are in respect to inlet cracking valve 46. As outlet valve cam follower 190 follows outlet valve cam track 150, hood 194 periodically contacts closure flexure 188, lifting it away from side arm 186 so that the flow control force provided by cracking flexure 182, added to the balance force developed by balance block 58, is transmitted to valve face 106b, thereby compressing flexible tubing 34 against pressure plate 94 with a cracking force. In this configuration, outlet cracking valve 52 is in its cracking mode.

As plunger 48 compresses pumping portion 34b of the flexible tubing against pressure plate 94, the pressure developed by liquid trapped between inlet cracking valve 46, which is closed, and outlet cracking valve 52 acts on valve face 106b, in opposition to the cracking force produced by cracking flexure 182 and balance block 58. As the force developed by the fluid pressure reaches a predetermined level sufficient to cause outlet cracking valve 52 to pivot open slightly, liquid 31 flows past the outlet cracking valve from pumping portion 34b of the flexible tubing. Liquid 31 is thus delivered by volumetric pump 30 at a predefined cracking pressure.

A first form of flow detector 54 comprises a strain gauge 198, which is mounted on cracking flexure 182. Strain gauge 198 develops an output signal corresponding to the stress developed in cracking flexure 182, and therefore indicates that outlet valve arm 180 is rotating to allow fluid flow past outlet cracking valve 52. Accordingly, the signal developed by strain gauge 198 is indicative of whether fluid is being pumped through distal portion 34c of the flexible tubing as a result of displacement by plunger 48. If pumping portion 34b of the flexible tubing contains a relatively large proportion of air or other compressible gaseous fluid, plunger 48 cannot develop sufficient fluid pressure to overcome the cracking force exerted by cracking flexure 182 and balance block 58. As a result, strain gauge 198 fails to detect the stress of cracking flexure 182 that would have occurred if outlet valve arm 180 had pivoted open to allow fluid flow past outlet cracking valve 52 during a pumping stroke of plunger 48. Accordingly, the signal from strain gauge 198 is used to detect whether container 32 has run dry, allowing air to fill pumping portion 34b of the flexible tubing, or whether the flow of liquid 31 through volumetric pump 30 has otherwise been interrupted. The signal produced by strain gauge 198 is proportional to the movement of outlet valve arm 180. This fluid flow signal is used in the method of the present invention to determine whether to stop volumetric pump 30 and initiate an alarm when the expected fluid flow is not obtained, thereby alerting medical personnel of the problem so that it can be corrected.

Proximal pressure sensor 44 comprises a block 204, which is spring-biased into contact with proximal portion 34a of the flexible tubing and is disposed between inlet cracking valve 46 and balance block 42. A spring-bias force for proximal pressure sensor 44 is provided by two pairs of longitudinally extending flexures 202, disposed on each side of plunger 48. Flexures 202 are connected to support plates 266 on frame 100 by fasteners 206 at about the midpoint of the flexures. One of the four flexures 202 connecting block 204 to support plates 266 includes a strain gauge 200, which responds to stress developed in that flexure 202 as a function of fluid pressure within proximal portion 34a of the flexible tubing. As the fluid pressure increases within this portion of flexible tubing 34, flexures 202 connected to block 204 experience increased stress, producing a corresponding change in the output signal from strain gauge 200.

Similarly, distal pressure sensor 56 comprises a block 210, which is connected to the other ends of flexures 202. A strain gauge 208 is disposed on one of the four flexures, intermediate block 210 and one of the support plates 266. Strain gauge 208 produces a signal corresponding to the fluid pressure within distal portion 34c of the flexible tubing, based upon stress developed in flexures 202 as a result of that pressure. Distal pressure sensor 56 can be used to determine if distal portion 34c of the flexible tubing has been kinked, interrupting fluid flow through flexible tubing 34, for example, as might occur if a patient rolled over onto flexible tubing 34. Such a condition causes a notable increase in the distal fluid pressure that triggers an alarm and shuts off volumetric pump 30. If distal pressure sensor 56 should fail, flow detector 54 will also detect obstruction of fluid flow through distal portion 34c of the flexible tubing in response to a cessation of fluid flow from volumetric pump 30.

In FIGS. 5, 6, and 7, details of tubing shapers 50a and 50b are disclosed. Since it is preferable to use relatively low cost PVC tubing in connection with volumetric pump 30, tubing shapers 50a and 50b are provided to ensure consistent operation and volumetric capacity of pumping portion 34b of the flexible tubing throughout the entire operating range of volumetric pump 30. At relatively high pumping rates, PVC tubing does not fully recover to its normal round uncompressed shape from a compressed condition rapidly enough to fill completely with fluid. Accordingly, the volumetric displacement of fluid within the PVC tubing that occurs with each pumping stroke is less than desired. To avoid this problem, tubing shapers 50a and 50b force pumping portion 34b of the flexible tubing to recover rapidly to its maximum volumetric capacity, i.e., to open sufficiently so that the desired amount of liquid 31 fills the pumping chamber defined by pumping portion 34b of the flexible tubing.

Each tubing shaper 50a and 50b comprises an angled arm 234, terminating at one end in a longitudinally extending jaw 236. Arms 234 are attached to frame 100 at pivot mounts 230, about which arms 234 rotate as tubing shaper rollers 160 roll along inner surfaces 232 of arms 234. Thus, the reciprocating up-and-down motion of plunger 48 along its reciprocation axis inherently acts on tubing shaper rollers 160 in "lock-step", causing jaws 236 to pinch pumping portion 34b of the flexible tubing at the proper time, thereby reforming flexible tubing 34 into the required pumping volume or capacity as plunger 48 lifts away from pressure plate 94.

In FIG. 5, tubing shapers 50a and 50b are shown moving in opposite directions, away from pumping portion 34b of the flexible tubing as plunger 48 descends to compress flexible tubing 34, displacing fluid from pumping portion 34b. However, in FIG. 6, plunger 48 is shown moving upwardly away from pressure plate 94, acting on tubing shaper rollers 160 to force opposing jaws 236 to swing inwardly toward each other in order to reshape pumping portion 34b of the flexible tubing so that it achieves its desired volumetric capacity.

To further enhance the repeatability and consistency of the volumetric capacity defined in pumping portion 34b of the flexible tubing, plunger cam track 152 is sized and shaped so that plunger 48 never completely compresses pumping portion 34b of the flexible tubing, even at the lowermost point of the plunger's reciprocal stroke. In addition, at the top of its reciprocal stroke, plunger 48 remains in contact with pumping portion 34b of the flexible tubing. The range of diametrical compression of flexible tubing 34 is from about 15% at the top of the pumping stroke to about 85% at the bottom of the pumping stroke of plunger 48. Since flexible tubing 34 need not recover to a fully uncompressed condition, i.e., to a perfect circular cross section, changes in the elasticity of flexible tubing 34 due to continued use and repeated compression have much less effect on the volumetric capacity of pumping portion 34b of the flexible tubing than would otherwise occur.

In order to calibrate tubing shapers 50a and 50b so that their range of motion corresponds to that required to achieve proper reshaping of pumping portion 34b of the flexible tubing, a wedge-shaped slot 240 is provided in the upper outer portion of arms 234. To adjust the angle between the upper and lower portions of each arm 234, a wedge-shaped insert 238 is driven into wedge-shaped slot 240, deflecting the upper portion of arm 234 through an angle, as indicated by reference numeral 242. Angle 242 is determined by use of an appropriate calibration jig (not shown) during manufacture of tubing shapers 50a and 50b, or during assembly of these components in volumetric pump 30.

Details of inlet cracking valve 46 are shown in FIG. 8, and details of outlet cracking valve 52 are shown in FIG. 9. In these drawings, it is apparent that downwardly depending pivot arms 136 straddle flexible tubing 34, and are spaced apart sufficiently so that blocks 204 and 210 of proximal pressure sensor 44 and distal pressure sensor 56 can fit therebetween. FIG. 8 more clearly illustrates side arm 116 and V-shaped side arm 118 at the top of inlet valve arm 108. In FIG. 9, the specific disposition of side arm 186 in respect to outlet valve cam follower 190, closure flexure 188, and cracking flexure 182 is also more clearly shown.

One of the advantages of using flat metal spring flexures, i.e., cracking flexure 112 and closure flexure 120, for biasing inlet valve arm 108 is that the force provided by each of these flexures is much more readily controlled than is typically the case with other types of spring assemblies. For example, by trimming the shape of these flexures or selecting flexures of a different thickness, the spring force they produce (i.e., their spring constant, K) can be readily modified and consistently controlled. The same advantages apply to the other flexures used in volumetric pump 30, such as inlet follower flexure 128 and balance block flexures 110. Accordingly, the cracking pressure and other characteristics of volumetric pump 30 can be precisely determined.

Figure 11:
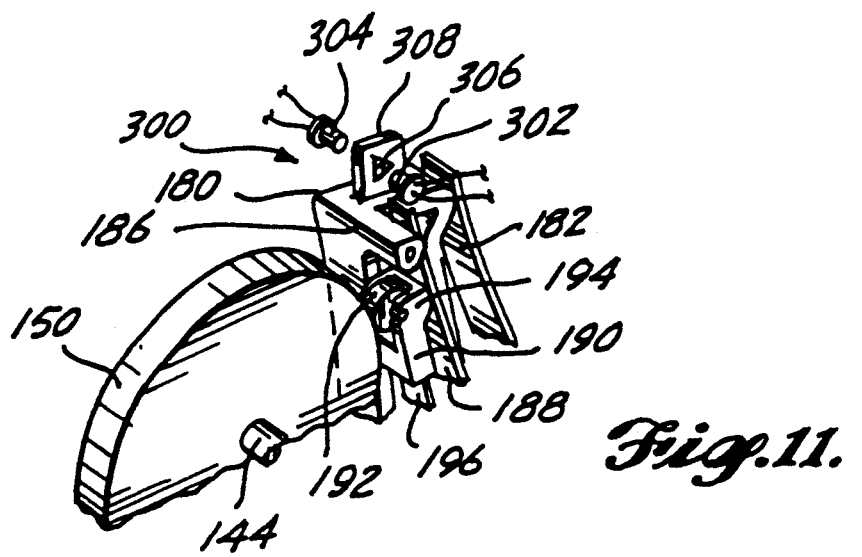
FIG. 11 illustrates another type of sensor used in connection with the present invention and shows a portion of the outlet cracking valve arm.

Instead of using strain gauge 198 to sense stress in cracking flexure 182 as outlet cracking valve 52 opens, other types of sensors may be mounted adjacent outlet valve arm 180 to produce a signal indicative of its pivotal motion. For example, the pivotal movement of outlet valve arm 180 as fluid flows past outlet cracking valve 52 can be detected using an optical sensor 300, as shown in FIG. 11. To accommodate optical sensor 300, the upper end of outlet valve arm 180 is modified to include a tab 308. Centered within tab 308 is a triangular shaped aperture 306. Disposed on opposite sides of tab 308 are a light emitting diode (LED)302 and a phototransistor 304. Light emitted by LED 302 passes through triangular shaped aperture 306 and is picked up by phototransistor 304. When outlet cracking valve 52 is closed, only a very small portion of phototransistor 304 is illuminated by light from LED 302 through the apex of triangular shaped aperture 306. However, as outlet valve arm 180 moves because of fluid flow past outlet cracking valve 52, the amount of light emitted by LED 302 that reaches phototransistor 304 increases, since the light can pass through the larger area of triangular shaped aperture 306 adjacent its base. Accordingly, the signal produced by phototransistor 304 serves to indicate whether outlet valve arm 180 has moved to permit fluid flow from volumetric pump 30.

Figure 12:
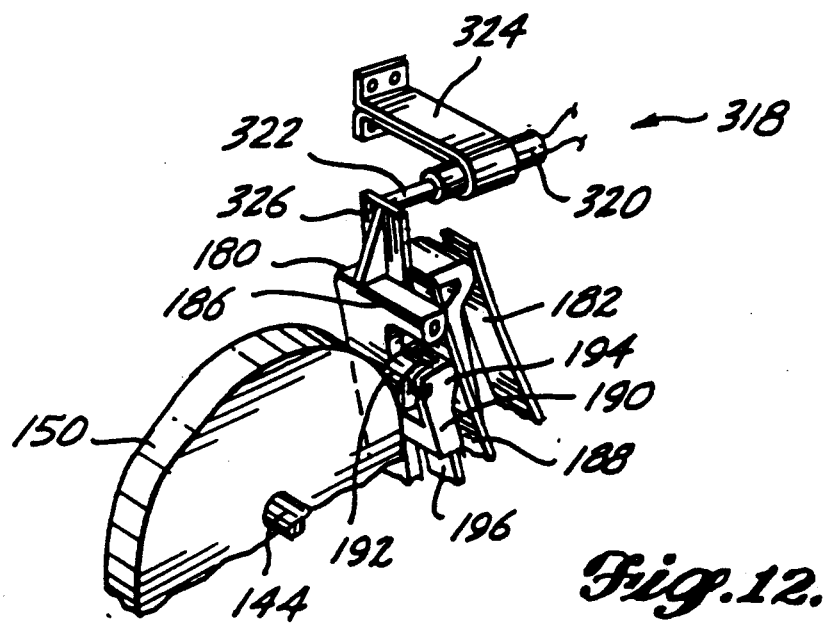
FIG. 12 illustrates yet another type of sensor used in connection with the present invention and a portion of the outlet cracking valve arm.

In FIG. 12, a linear variable displacement transformer (LVDT) 318 is used to detect whether outlet valve arm 180 has moved to allow fluid flow from volumetric pump 30 past outlet cracking valve 52. In this form of the flow detector, the upper end of outlet valve arm 180 is modified to include a transverse tab 326. Tab 326 abuts against a ferrous metal core 322, which extends from the center LVDT 318. LVDT 318 also comprises a plurality of electromagnetic coils 320 including a primary coil and two secondary coils (not separately shown). As ferrous metal core 322 is forced further into-magnetic coils 320 by tab 326 as outlet cracking valve 52 opens, the ferrous metal core increases the extent of magnetic coupling between the -magnetic coils, changing the signal LVDT 318 produces. A bracket 324 supports -magnetic coils 320 at a fixed position with respect to the movement of ferrous metal core 322. A helical coil spring (not shown) inside LVDT 318 biases ferrous magnetic core 322 into contact with tab 326.

It is also contemplated that a Hall sensor could be mounted adjacent outlet valve arm 180 to detect the motion of a magnet bonded to the outlet valve arm, as outlet cracking valve 52 opens to enable fluid flow from volumetric pump 30. In addition, flow detector 54 may also comprise a variable capacitor that changes capacitance value as outlet valve arm 180 pivots. LVDT 319 and a variable capacitor are simply different types of variable reactance sensors. Clearly, those of ordinary skill in the art will recognize that these and other types of sensors for detecting motion of outlet valve arm 180 can serve to produce a signal indicative of fluid flow from volumetric pump 30 for use in connection with the present invention.

Figure 13:
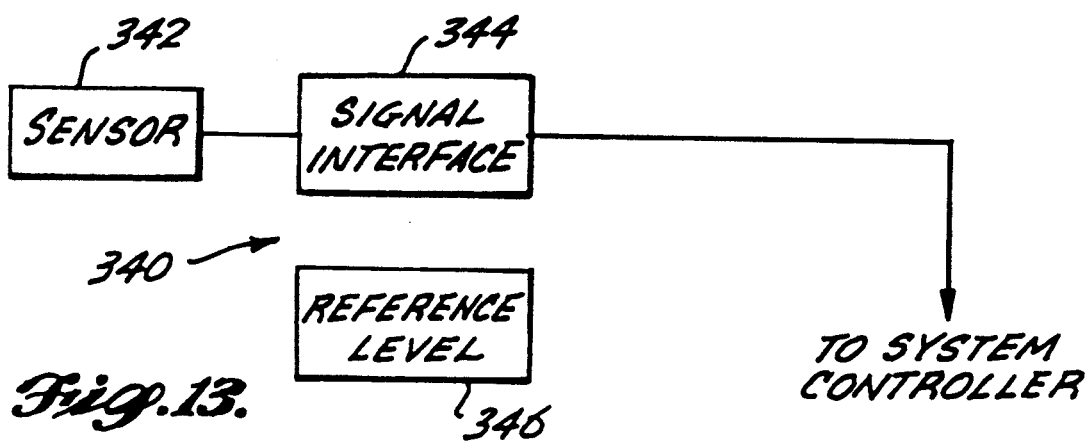
FIG. 13 is a schematic block diagram of a circuit used in connection with the sensor for producing a signal indicative of fluid flow from the volumetric pump.

FIG. 13 illustrates a circuit 340 that is used in connection with strain gauge 198, optical sensor 300, LVDT 318, or with the alternative sensors that can comprise flow detector 54 (as discussed above) to produce a signal indicative of movement of outlet valve arm 180 and thus indicative of fluid flow from volumetric pump 30. As shown in FIG. 13, a sensor block 342 produces a signal indicating whether outlet valve arm 180 has moved to enable fluid flow from the volumetric pump. The signal produced by the sensor in block 342 is input to a signal interface 344. The function performed by interface 344 depends upon the type of sensor used to monitor the motion of outlet valve arm 180. For example, if optical sensor 300 is employed, signal interface 344 comprises a simple amplifier used to amplify the signal from photo transistor. However, if LVDT 318 is employed, signal interface 344 comprises a differential amplifier that produces a signal indicative of the difference in electromagnetic coupling between the primary coil and two secondary coils comprising -magnetic coils 320 as ferrous metal core 322 is moved into the center of the LVDT. A signal output from signal interface 344 comprises an analog DC level that is input to a control 400 shown in FIG. 14.

Figure 14:
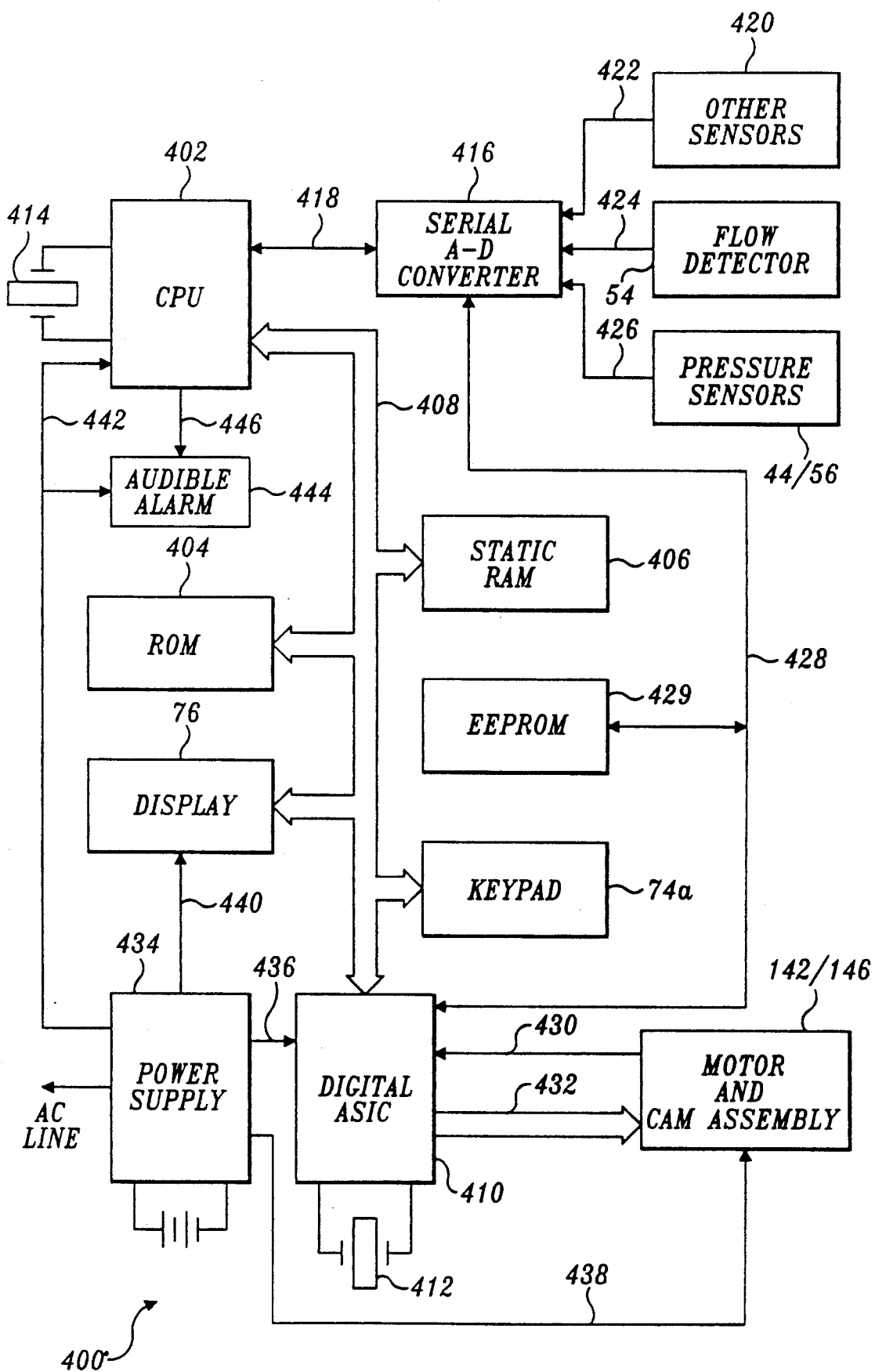
FIG. 14 is a schematic block diagram illustrating a volumetric pump controller that is responsive to a signal output from the sensor circuit of FIG. 13 in carrying out the method of the present invention.

FIG. 14 schematically illustrates a control 400, which is electronically connected to control panel 74 to respond to operator selection of input data provided thereby and to display data and alarm conditions to the operator on display 76, in addition to controlling the operation of volumetric pump 30. In respect to the present invention, control 400 responds to the signals produce by flow detector 54 in monitoring whether fluid flow is occurring from volumetric pump 30. Control 400 includes a central processing unit 402, a nonvolatile read only memory (ROM) circuit 404 in which are stored program instruction for controlling volumetric pump 30, and a static random access memory (RAM) circuit 406 in which data developed during the operation of the pump are temporarily stored. ROM circuit 404 also stores the program code that controls determination of fluid from the volumetric pump in accordance with the steps of the present invention. ROM circuit 404 and RAM circuit 406 are electronically connected to CPU 402 by a combined bidirectional, eight-bit wide address/data/control bus 408. CPU 402 comprises an 8 MHz NEC Type V25 microcomputer circuit, having a 16 MHz crystal 414 to provide a time base, in the preferred form of the invention. Bus 408 is also connected to convey control signals, data, and address information to display 76 and to a digital application specific integrated circuit (ASIC) 410. A 3.2 MHz crystal 412 provides a time base for ASIC 410.

ASIC 410 is not required for monitoring fluid flow from the volumetric pump; the primary advantage of ASIC 410 in volumetric pump 30 relates to the control of motor 146, which drives cam assembly 142. Accordingly, a description of the design details of the ASIC is not required for an enabling disclosure of the method for detecting fluid flow implemented by control 400.

An eight channel, eight-bit serial along-to-digital (A-D) convertor 416 converts the analog signals from a plurality of sensors to digital signals that can be used by CPU 402. For example, other sensors 420, which are not related to the present invention, supply analog signals to A-D convertor 416 over signal leads 422. Of greater relevance to the determination of fluid flow, flow detector 54 supplies analog signals indicative of fluid flow from the volumetric pump 30 over signal lead 424. As explained above, these analog signals are produced by strain gauge 198 or by the other types of alternative flow detectors discussed above. The analog signals are processed by circuit 340 before being supplied to A-D convertor 416. A-D convertor 416 converts the analog signal to a corresponding digital signal under the control of CPU 402, which supplies control signals to the A-D convertor over a control lead 418. A lead 428 carries serial clock, serial data-in, and serial data-out between ASIC 410 and A-D convertor 416. Thus, the digital signal corresponding to the go/no-go signal indicative fluid flow from volumetric pump 30 is supplied in serial format to ASIC 410 over lead 428. ASIC 410 converts the serial signals to parallel format for use by CPU 402. Alternatively, a parallel A-D convertor could be used, eliminating the need for ASIC 410 to convert the format of the signals. The step carried out by CPU 402 in determining whether fluid is flowing from the volumetric pump are based upon the digital signal corresponding to the output signal of flow detector 54, as described in detail below.

As noted above, the principle advantage of ASIC 410 in volumetric pump 30 is in controlling motor 146. ASIC 410 is connected to supply control signals to motor 146 over leads 432. A lead 430 conveys motor and cam assembly position signals back to ASIC to provide feedback indicating the rotational position of cam assembly 142, which is important in determining when proximal and distal pressure signals are monitored during the pumping cycle of volumetric pump 30.

Control 400 includes a combination battery/AC line energized power supply 434. Appropriate DC power supply voltages are provided to each of the components of control 400 that require electrical power by power supply 434 over several power leads, including a lead 436, which conveys power to ASIC 410. Similarly, leads 438, 440, and 442 carry power to motor 146, display 76, and CPU 402, respectively. Lead 442 also conveys power to an audible alarm 444, which is controlled by CPU 402 in response to signals provided over a lead 446. Audible alarm 444 is used to alert an operator of volumetric pump 30 when an occlusion, cessation of fluid flow, air-in-line, or some other operating fault has occurred that requires corrective action by and operator.

Flow Detection Method

Figure 15B:
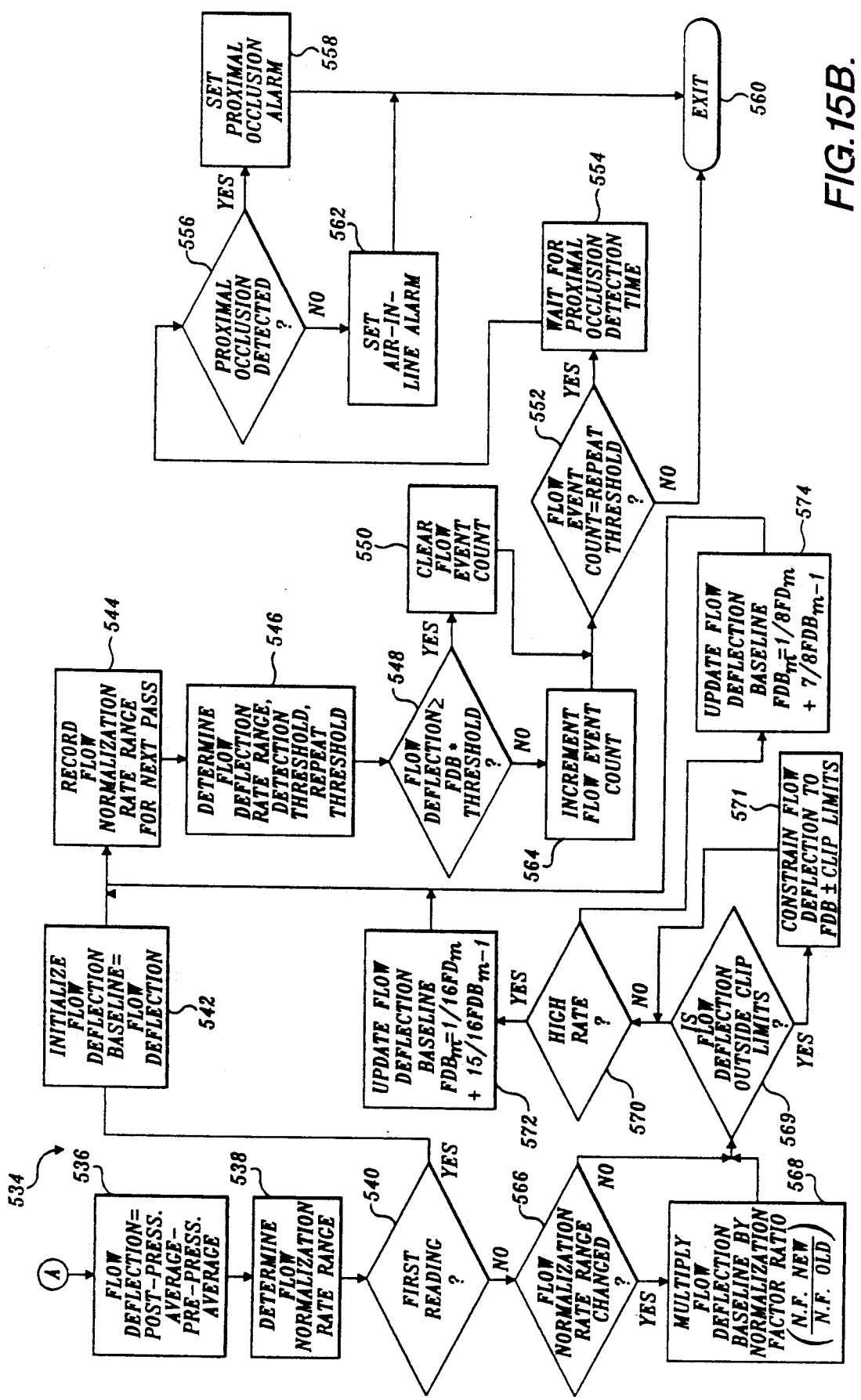

Turning now to FIGS. 15A and 15B, the steps implemented in carrying out the method for determining whether fluid is flowing from volumetric pump 30 are disclosed. In FIG 15A, a flow chart 500 starts at a block 502, which initiates monitoring of motor revolutions. In the preferred embodiment, 24 revolutions of motor 146 correspond to one complete revolution of cam assembly 142, and, thus, one pumping cycle. As noted above, feedback signals indicative of the number of revolutions in motor 146 and of the home position of cam assembly 142 are developed within volumetric pump 30. CPU 402 is thus provided with data indicating the relative progress of volumetric pump 30 through each of its pumping cycles. Revolution zero of the motor begins at the coincidence of the home positions of motor 146 and of a cam assembly 142, and ends one MOTOR_HOME pulse later, at the beginning of motor revolution one.

In a decision block 504, the algorithm determines whether the motor is at one of the pre-pressurization positions (corresponding to revolutions 17, 18, and 19 in the preferred embodiment). Assuming that the response to discussion block 504 is positive, a block 506 instructs CPU 402 to read the flow sensor signal. Thereafter, a decision block 507 determines if the motor is at the first pre-pressurization position (revolution 17) and, if so, a block 508 sets a pre-pressurization accumulation value equal to the current flow sensor signal reading. Thereafter, the program proceeds to an exit block 510.

A negative response to decision block 507 leads to a block 512, which adds the current pre-pressurization reading to a pre-pressurization accumulation. If the pumping cycle has advanced to the last pre-pressurization reading position (revolution 19), as determined by a decision block 514, a block 516 instructs the CPU to calculate a pre-pressurization average, which is equal to the pre-pressurization accumulation divided by the number of pre-pressurization reading position (three). Thereafter, of following a negative response to decision block 514, the algorithm proceeds to exit block 510.

Referring back to decision block 504, a negative response leads to a decision block 518, which determines whether volumetric pump 30 is operating at a high flow rate. In the preferred embodiment, the high flow rate is any nominal flow greater than 125 milliliters per hour. A positive response to decision block 518 leads to a decision block 520, which determines whether the pumping cycle has progressed to of the high rate post-pressurization positions, corresponding to revolutions two, three, four, five, and six of motor 146. If so, CPU 402 is instructed by block 522 to read the flow sensor signal. Thereafter, a decision block 524 determines whether the pumping cycle is at the first high rate post-pressurization position (revolution two), and, if it is, a block 526 sets the post-pressurization accumulation equal to the current flow sensor signal reading. Thereafter, the algorithm proceeds to exit block 510.

If the response to decision block 518 is negative, i.e., that the pump is operating at its Lo rate, A negative response to decision block 524 leads to a block 528, which adds the current flow sensor signal reading to the existing post-pressurization accumulation. Then, a decision block 530 determines if the pumping cycle has progressed to the last post-pressurization position (revolution six of motor 146) and, is so, a block 532 determines a post-pressurization average, which is equal the post-pressurization accumulation divided by the total number of positions at which such readings were taken (five). The logic then continues to FIG. 15B (reference A on both FIGS. 15A and 15B) where a flow chart 534 begins with a block 536. In block 536, a value for a flow deflection is established, which is equal to the difference between the post-pressurization average and the pre-pressurization average (the later being determined in steps yet to be discussed). Thereafter, a block 538 determines the flow normalization rate range. In the preferred embodiment, there are three flow normalization rate ranges, corresponding respectively to one through 39 milliliters per hour, 40 through 79 milliliters per hour, and 80 through 999 milliliters per hour.

A decision block 540 determines if a first flow deflection reading is being made in the current pumping sequence, and, if it is, a block 542 initializes the flow deflection baseline to equal the current flow deflection, which was determined in block 536. Thereafter, a block 544 records the flow normalization rate range for the next pass through the algorithm.

Block 546 then determines flow deflection rate range, detection thresholds, and repeat thresholds, which correspond to the values shown in Table I:

TABLE I

| Rate Milliliters/Hr | Detection Threshold | Repeat Threshold |
|---|---|---|
| 1-10 | 90% | 2 |
| 11-50 | 85% | 2 |
| 51-124 | 80% | 3 |
| 125-200 | 75% | 4 |
| 201-500 | 73% | 5 |
| 501-999 | 70% | 5 |

Based upon the flow deflection rate range, each of the other two variables, detection threshold and repeat threshold, are determined using a look-up table with the same information shown in Table I above. In a decision block 548, CPU 402 determines if the flow deflection value is greater than the flow deflection baseline times the threshold. If it is, a block 550 clears the flow event counter. However, if not, the flow event counter is incremented by one count. Following block 550, a decision block 552 determines if the flow event counter is equal to the repeat threshold (reference Table I). If it is, the algorithm would ordinarily provide a flow interruption detection alarm. However, since the flow interruption could be caused either by air bubbles within pumping section 34b of the flexible tubing or by a proximal occlusion, the algorithm waits until a proximal occlusion would be detected in the pumping cycle to determine which of the two causes of flow interruption have occurred. If the flow event counter dose not equal the repeat threshold, the algorithm proceeds to an exit block 560.

After block 554, a decision block 556 determines if a proximal occlusion has been detected, and, if it has, a block 558 sets the proximal occlusion alarm, thereby indicating the source of the flow interruption. Alternatively, if a proximal occlusion has not been detected, a block 562 sets the air-in-line alarm. Since volumetric pump 30 is incapable of developing a cracking pressure in pumping portion 34b sufficient to force the compressed gaseous fluid past the outlet cracking valve, fluid flow from the volumetric pump is interrupted when a substantial portion of the fluid within a pumping portion of the flexible tubing is air or other gas. Although the volumetric pump is also provided with an air-in-line sensor, flow detection in accordance with the present invention serves as a backup to ensure that an air embolism dose not occur. The air-in-line sensor serves the additional function of detecting if the fluid flowing from volumetric pump 30 comprises excessive air bubbles, which may not be of sufficient volume to interrupt fluid flow from the pump.

Although block 558 provides for setting the proximal occlusional alarm in the event that a proximal occlusion is detected, it should also be apparent that a flow interruption alarm could be set independent of the proximal occlusion alarm. Accordingly, the present method has application to a pump in which proximal occlusion is not separately detected. Following block 558, the algorithm proceeds to exit block 560.

Referring back to decision block 540, in the event that the reading is not the first in the pumping sequence, a decision block 566 determines if the flow normalization rate range is changed. If it is not, the logic proceeds to decision block 569, which determines if the flow deflection is outside the clip limits (plus or minus 10% of the existing FDB value). An affirmative response causes the flow deflection to be limited to the current value of FDB plus the clip limit or minus the clip limit, as appropriate, as indicated in a block 571. If the flow deflection is not outside the acceptable range or after it is limited as provide in block 571, the algorithm proceeds to a decision block 570 that determines if the pump is operating at its Hi pumping rate.

If the rate range is different in decision block 566, a block 568 multiplies the flow deflection baseline by a normalization factor ratio, which is equal to the normalization factor for the new range divided by the normalization factor for the old range. In the preferred embodiment, the normalization factors used are: 1.15 for one through 39 milliliters per hour; 1.08 for 40 through 79 milliliters per hour; and, 1.00 for 80 through 999 milliliters per hour. The algorithm then proceeds with decision block 570 to determine if the volumetric pump is operating at its high delivery rate (greater than 125 milliliters per hour) and, if so, a block 572 updates the flow deflection baseline, setting it equal to one-sixteenth of the flow deflection value plus fifteen-sixteenths of the previous flow deflection baseline. The logic then proceeds to block 544. However, if the volumetric pump is not operating at the high pumping rate, a block 574 sets the flow deflection baseline equal to one-eight of the current flow deflection reading plus seven-eights of the previous flow deflection baseline before proceeding to block 544.

Tuning back to FIG. 15A, flow chart 500, a negative result to decision block 518, which determines whether the pump is operating at a high pumping rate, leads to a decision block 576, which determines if the pumping cycle is at one of the low rate post-pressurization positions. In the preferred embodiment, the low rate post-pressurization positions include revolutions zero through six of motor 146. If so, a block 578 causes CPU 402 to read the flow sensor signal.

A decision block 580 then determines if the pressurization cycle is at the first post-pressurization position (at revolution zero), and, if so, block 582 sets the post-pressurization accumulation equal to the current flow sensor signal reading. The algorithm then proceeds to exit block 510.

Assuming a negative response to decision block 580, a block 584 adds the current flow sensor signal reading to the previous post-pressurization accumulation value, and a decision block 586 determines whether the pumping cycle is at the last post-pressurization position. Assuming a positive response to this inquiry, block 588 sets the post-pressurization average equal to the post-pressurization accumulation divided by the total number positions at which the reading were taken (seven) before proceeding on to block 536 on flow chart 534 in FIG. 15B. A negative response to decision block 586 cause the algorithm to proceed to exit block 510.

Figure 16:
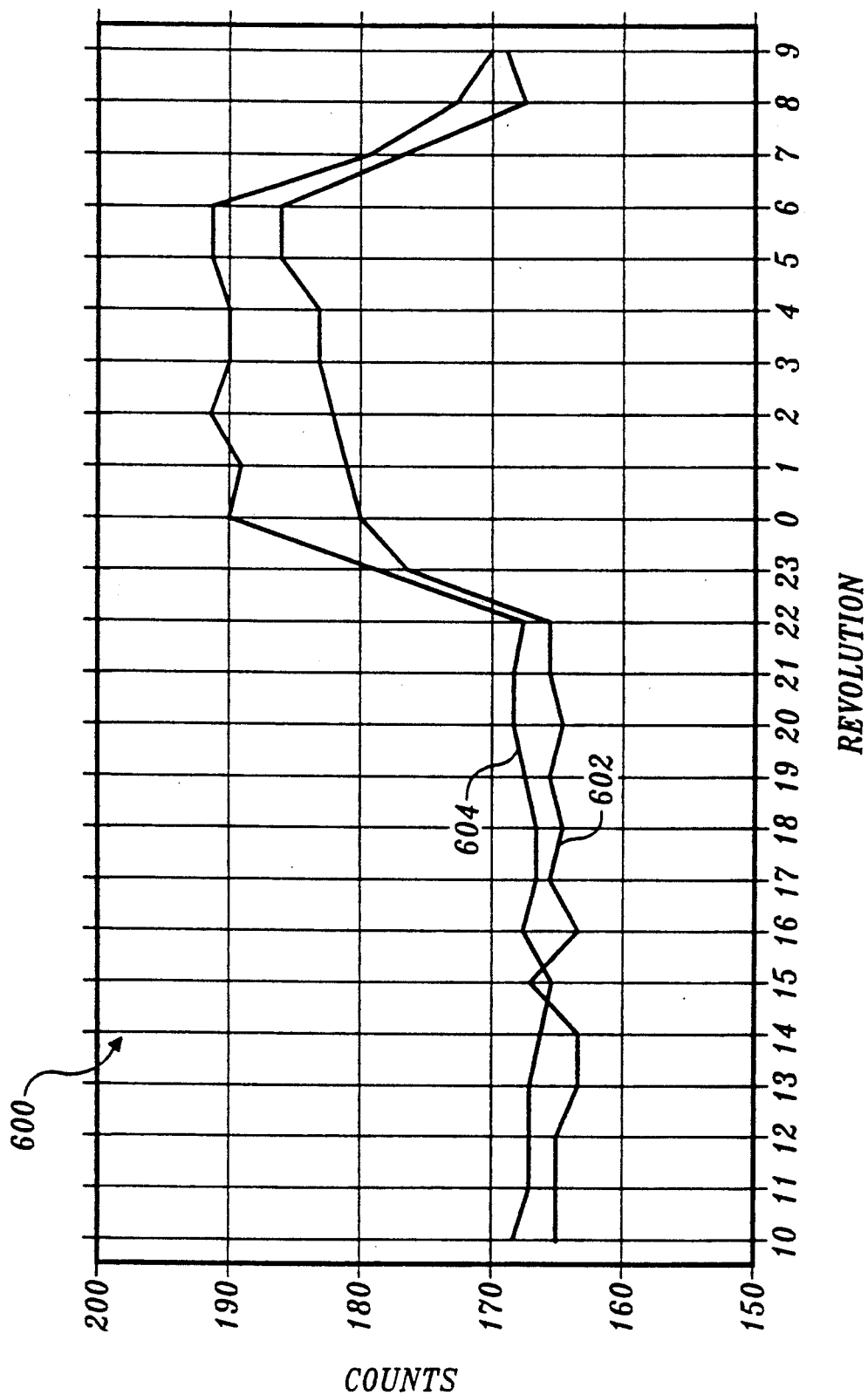
FIG. 16 is graph of the relative amplitude of the flow sensor signal at a nominal fluid flow rate of 10 ml/hr., for both water and air, as a function of revolutions of a motor that drives the volumetric pump, during one pumping cycle.

Referring to FIG. 16, a graph 600 illustrates the flow detector signal in terms of counts produced by the analog-to-digital converter for both air (a trace 602) and water (a trace 604) input to volumetric pump 30. For the data in this FIGURE, the volumetric pump is set for a nominal flow rate of 10 milliliters per hour. Pressurization of the fluid within pumping portion 34b of the flexible tubing begins at approximately revolution 21. Compression of the pumping portion continues until the plunger reaches its maximum compression position at approximately revolution 9. Since volumetric pump 30 is operating at a low pumping rate, i.e., at less than 200 milliliters per hour, the difference between the average of the flow sensor signal counts at revolutions zero through six and the average of the flow sensor counts at revolutions 17 through 19 determines the flow deflection. The flow deflection is used to update the deflection baseline weighted average. Subsequently, if the flow deflection is less than the flow deflection baseline multiplied by the detection threshold (0.9 for this range), the flow event counter is incremented. Furthermore, if the total number of consecutive flow interrupted events counted equals two, the algorithm detects a cessation of flow from volumetric pump 30. As a result, the algorithm is able to detect the difference in the count for air, which is incapable of developing the cracking pressure within pumping portion 34b of the flexible tubing. Consequently, even though the absolute difference between the number of counts from the flow detector for air and for water is relatively small, the algorithm can detect the absence of flow the volumetric pump when it is trying to pump air.

Figure 17:
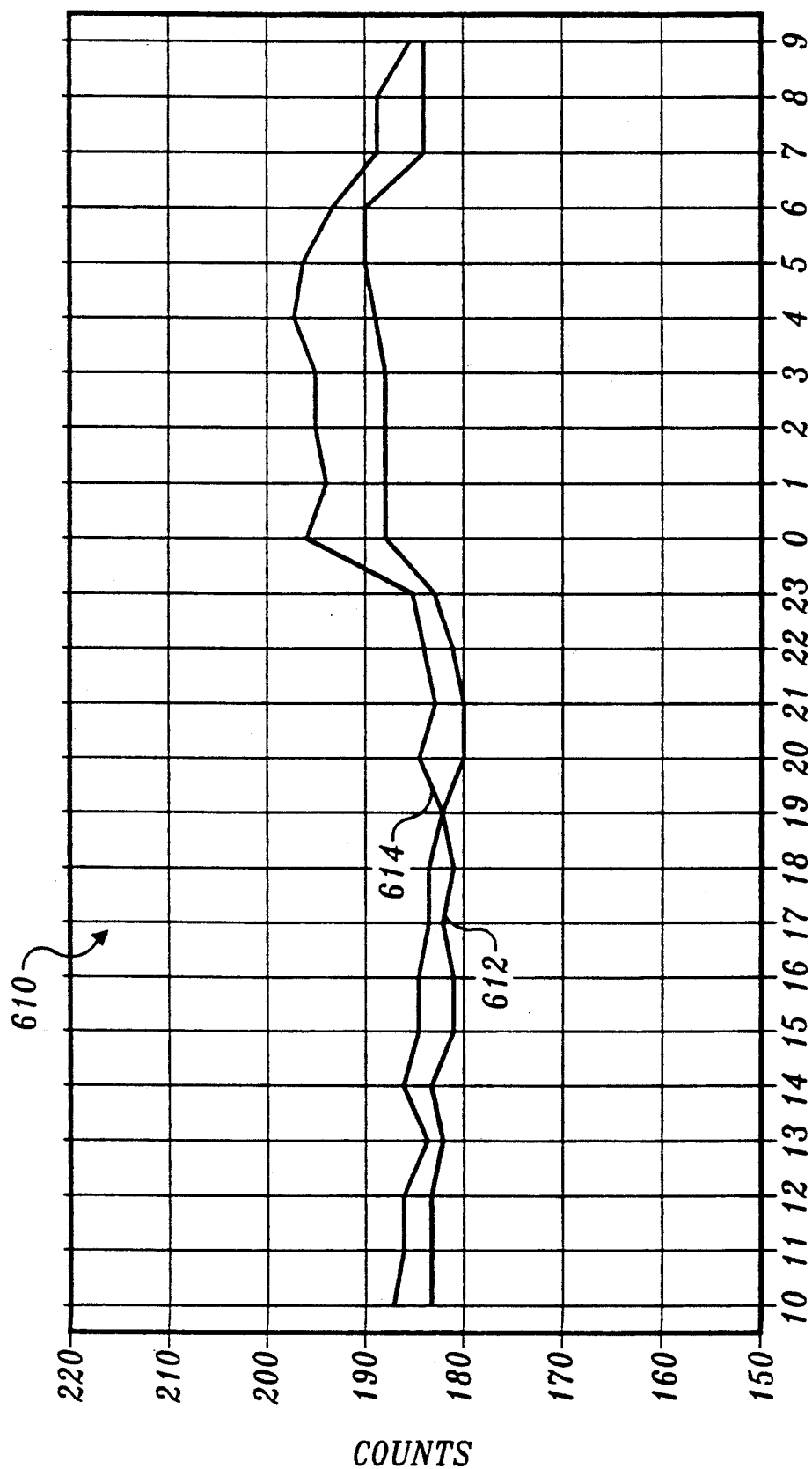
FIG. 17 is graph of the relative amplitude of the flow sensor signal at a nominal fluid flow rate of 400 ml/hr/., for both water and air, as a function of revolutions of a motor that drives the volumetric pump, during one pumping cycle.

In FIG. 17, a graph 610 illustrates the flow detector sensor output for air, (a trace 612), and for water (a trace 614). For these traces, the volumetric pump is set to deliver 400 milliliters per hour.

Figure 18:
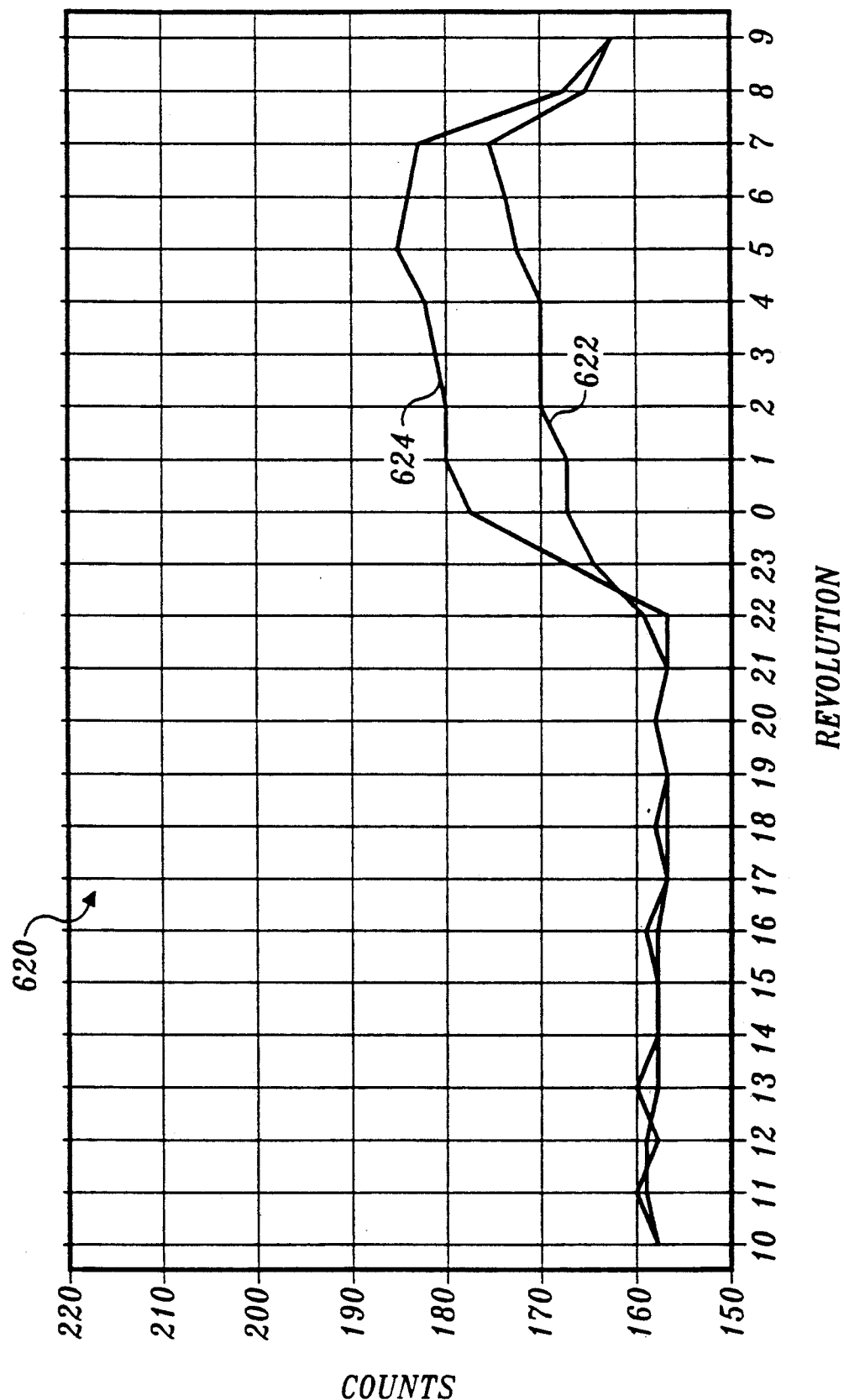
FIG. 18 is graph of the relative amplitude of the flow sensor signal at a nominal fluid flow rate of 999 ml/hr., for both water and air, as a function of revolutions of a motor that drives the volumetric pump, during one pumping cycle.

Similarly, in FIG. 18, a graph 620 depicts the relative amplitudes in count of the signals produced by the flow detector for volumetric pump 30 when filled with air (a trace 622) and when filled with water (a trace 624). Volumetric pump 30 is set to a flow rate of 999 milliliters per hour to produce these data, and, in both cases, after flexible tubing 34 had been installed in volumetric pump 30 for five minutes prior to the pumping cycle depicted. Since the flexible tubing experiences change in elasticity over approximately the first thirty minutes after it is installed in the volumetric pump and subjected to compression, it is important that the algorithm used for determining flow flow the pump adapt for changes that may result as the flexible tubing relaxes and stabilizes over its initial period of use. The use of a weighted average in determining the baseline accommodates changes is elasticity of the flexible tubing after it is first installed.

While the preferred embodiment of the invention has been illustrated and described, it will be appreciated that various changes can be made therein without departing from the spirit and scope of the invention. Accordingly, it is not intended that the scope of the invention be limited by this disclosure, but instead, that it be determined by reference to the claims that follow.

The embodiments of the invention in which an exclusive property or privilege is claimed are defined as follows:

1. A method for determining whether fluid is flowing from a positive displacement pump, which includes an outlet valve that opens to allow fluid to flow past it during a pumping cycle, when a fluid pressure within the pump reaches a predefined cracking pressure, comprising the steps of:

producing a signal indicative of a movement of the outlet valve from a closed position to at least a partially open position that allows fluid to flow from the pump in response to the fluid pressure within the pump exceeding the predefined cracking pressure;

establishing an electrical threshold for the signal; comparing the signal to the threshold; and determining that fluid is not flowing from the pump based upon the relative magnitudes of the signal and the threshold.

2. The method of claim 1, wherein the step of establishing the threshold comprises the steps of:

a. determining a pre-pressurization level of the signal during the pumping cycle at a first time interval that is substantially prior to pressurizing the fluid to the cracking pressure;

b. determining a post-pressurization level of the signal during the pumping cycle at a second time interval that is substantially after pressurizing the fluid to the cracking pressure; and c. determining a difference between the post-pressurization level and the pre-pressurization level, the threshold being a function of said difference.

3. The method of claim 2, wherein the pre-pressurization level is an average of a plurality of pre-pressurization readings taken at a plurality of times during the first time interval.

4. The method of claim 2, wherein the post-pressurization level is an average of a plurality of post-pressurization readings taken at a plurality of times during the second time interval.

5. The method of claim 1, further comprising the step of compensating the threshold for variations in the signal as a function of a rate at which the pump delivers fluid.

6. The method of claim 1, further comprising the step of producing an alarm signal if the relative magnitude of the signal and the threshold indicates that fluid is not flowing from the pump.

7. The method of claim 6, wherein the step of producing the alarm signal occurs only if the relative magnitude of the signal and the threshold indicates that fluid is not flowing from the pump for a plurality of pumping cycles.

8. The method of claim 1, further comprising the step of determining whether fluid is not flowing from the pump due to an occlusion or due to the presence of a substantial volume of a gaseous fluid in the pump.

9. The method of claim 1, wherein pressurization of a substantially gaseous fluid by the pump can not develop a fluid pressure in excess of the cracking pressure, so that after the substantially gaseous fluid enters the pump, fluid flow from the pump is interrupted.

10. The method of claim 1, wherein the step of producing the signal comprises the step of monitoring a stress applied to a flexure that biases the outlet valve closed, to detect when the fluid pressure in the pump has exceeded the cracking pressure, since fluid flow from the pump occurs when the flexure is elastically deformed by the opening of the outlet valve.

11. A method for determining whether a liquid is flowing from an outlet of a positive displacement pump having an outlet valve that only opens to allow a fluid to flow from the pump when a pressure developed by the fluid exceeds a predefined cracking pressure, comprising the steps of:

a. applying a spring bias force to the outlet valve to develop a force that closes the outlet valve until the pressure of the fluid within the pump overcomes the force, causing the outlet valve to open sufficiently so that fluid flows from the pump;

b. sensing a movement of the outlet valve as fluid in the pump flows through the outlet valve after the pressure of the fluid exceeds the cracking pressure, forcing the outlet valve open, and by sensing the movement, producing a signal proportional to the opening of the outlet valve; and c. in response to the signal, determining whether the liquid is flowing from the pump through the outlet valve.

12. The method of claim 11, further comprising the step of producing an alarm in the event that a cessation of liquid flow from the pump is detected.

13. The method of claim 11, wherein the step of sensing comprises the step of monitoring a stress in a spring that produces the spring bias force to determine whether the spring has been strained by the opening of the outlet valve.

14. The method of claim 13, wherein step of producing the signal comprises the step of mounting a strain gauge on the spring so that it is sensitive to stress of the spring and produces the signal in response thereto.

15. The method of claim 11, further comprising the step of detecting whether a substantial quantity of a gaseous fluid is within the pump, causing a cessation of fluid flow from the pump, as a function of an occlusion signal.

16. The method of claim 11, wherein the step of determining whether liquid is flowing from the pump comprises the steps of determining a baseline level, and comparing a magnitude of the signal to the baseline level, interruption of liquid flow from the pump causing the magnitude of the signal to be less than the baseline level.

17. The method of claim 16, wherein the step of determining the baseline level comprise determining an average level of the signal prior to pressurization of the fluid, determining an average level of the signal after pressurization of the fluid, and a difference between said average levels.

18. The method of claim 17, wherein the step of determining the baseline level further comprises the step of compensating the baseline level for variations in the signal due to a pumping rate of the pump.

19. The method of claim 17, wherein the step of determining the baseline level further comprises the step of determining a weighted average of the baseline level during successive pumping cycles.

20. The method of claim 19, wherein a weighting factor applied to determine the weighted average differs as a function of a selected pumping rate of the pump.

* * * * *

UNITED STATES PATENT AND TRADEMARK OFFICE
CERTIFICATE OF CORRECTION

PATENT NO.   : 5,180,287
DATED        : January 19, 1993
INVENTOR(S)  : V. R. Natwick et al.

It is certified that error appears in the above-identified patent and that said Letters Patent is hereby corrected as shown below:

| COLUMN | LINE  |   |
|--------|-------|---|
| 4  | 18    | after "is" insert --a-- |
| 4  | 23    | after "is" insert --a-- |
| 4  | 24    | "ml/hr/." should read --ml/hr.-- |
| 4  | 28    | after "is" insert --a-- |
| 8  | 65    | "bearings 200" should read --bearings 220-- |
| 14 | 2     | "LVDT 319" should read --LVDT 318-- |
| 14 | 41    | "produce" should read --produced-- |
| 14 | 45    | "instruction" should read --instructions-- |
| 14 | 50    | after "fluid" insert --flow-- |
| 15 | 1     | "along-to-digital" should read --analog-to-digital-- |
| 15 | 26    | "step" should read --steps-- |
| 15 | 39    | after "Control 400" insert --also-- |
| 16 | 10    | "discussion" should read --decision-- |
| 16 | 25    | "position" should read --positions-- |
| 16 | 26    | "of" should read --or-- |
| 16 | 35    | after "to" insert --one-- |
| 16 | 46&47 | delete the entire phrase |
| 16 | 55    | after "equal" insert --to-- |

UNITED STATES PATENT AND TRADEMARK OFFICE
CERTIFICATE OF CORRECTION

PATENT NO. : 5,180,287
DATED : January 19, 1993
INVENTOR(S) : V. R. Natwick et al.

It is certified that error appears in the above-identified patent and that said Letters Patent is hereby corrected as shown below:

| | | |
|---|---|---|
| 17 | 39 | "dose" should read --does-- |
| 18 | 14 | "provide" should read --provided-- |
| 18 | 34 | "one-eight" should read --one-eighth-- |
| 18 | 35 | "seven-eights" should read --seven-eighths-- |
| 18 | 60 | after "number" insert --of-- |
| 18 | 61 | "reading" should read --readings-- |
| 18 | 63 | "cause" should read --causes-- |
| 19 | 27 | after "flow" insert --from-- |
| 19 | 45 | "flow" (second occurrence) should read --from-- |

Signed and Sealed this

Eighth Day of February, 1994

Attest:

BRUCE LEHMAN

*Attesting Officer*     *Commissioner of Patents and Trademarks*